United States Patent [19]
Masuda et al.

[11] 4,404,289
[45] Sep. 13, 1983

[54] METHOD FOR IMMUNOCHEMICAL MEASUREMENT OF TRACE COMPONENTS

[75] Inventors: Nobuhito Masuda; Shigeru Nagatomo; Yuji Mihara, all of Minami-ashigara, Japan

[73] Assignee: Fuji Photo Film Co., Ltd., Kanagawa, Japan

[21] Appl. No.: 298,719

[22] Filed: Sep. 2, 1981

[30] Foreign Application Priority Data

Sep. 2, 1980 [JP] Japan ............................. 55-120597
Sep. 2, 1980 [JP] Japan ............................. 55-120598

[51] Int. Cl.$^3$ ...................... G01N 33/54; G01N 33/52
[52] U.S. Cl. .................................... 436/538; 422/56; 422/57; 430/566; 435/4; 435/7; 435/805; 436/536; 436/544; 436/805; 436/807
[58] Field of Search ................. 23/230 B, 915; 424/8, 424/12; 435/4, 7; 430/566; 436/536, 538, 544

[56] References Cited

U.S. PATENT DOCUMENTS

| 3,782,949 | 1/1974 | Olivares | 430/566 X |
| 4,331,444 | 5/1982 | Mihara | 23/230 B |
| 4,337,063 | 6/1982 | Mihara | 23/230 B |
| 4,337,065 | 6/1982 | Hiratsuka | 23/230 B |

Primary Examiner—Sidney Marantz
Attorney, Agent, or Firm—Sughrue, Mion, Zinn, Macpeak, and Seas

[57] ABSTRACT

In an immunochemical measurement method of an antigen or antibody which comprises competitively reacting an antigen or antibody labelled with spectral sensitizer and an antigen or antibody to be measured, bringing either the reaction product of immune reaction or the unreacted component into contact with silver halide, exposing the same to light having a wavelength which the spectral sensitizer absorbs, developing the exposed silver, and, measuring optical density of the thus formed silver image and/or colored dye, the contact with silver halide is performed in the presence of a specific hydrazine compound. Thus, detection sensitivity is markedly improved.

8 Claims, No Drawings

METHOD FOR IMMUNOCHEMICAL MEASUREMENT OF TRACE COMPONENTS

BACKGROUND OF THE INVENTION

1. Field of the Invention

This invention relates to a method for immunochemical measurement of a trace component(s) using a spectral sensitizer as a photographically active substance.

2. Development of the Invention

Several methods for measuring a trace component(s) utilizing the combination of a photographically active substance and silver halide have been recently proposed by the present inventors. For example, methods in which a spectral sensitizer is employed as the photographically active substance are as follows:

(I) A method for immunologically measuring trace components which comprises:

competitively reacting an antigen or antibody labelled with a spectral sensitizer and an antigen or antibody to be measured with an antibody or antigen which specifically reacts with the antigen or antibody, bringing either the thus formed dye-labelled antigen-antibody reaction product or the unreacted antigen or antibody into contact with silver halide, exposing the same to a light having spectrally sensitizing wavelength corresponding to the spectral sensitizer, developing the exposed silver halide, and, measuring the resulting optical density of the developed silver and/or colored dye; and, (II) A method for analyzing the location or distribution of a corresponding antibody or antigen or its receptor in tissue, utilizing the same dye-labelled antigen or antibody as used in (I) above, in combination with silver halide, which is subjected to a specific immune reaction.

Radioimmunoassay (hereafter merely "RIA") is a method for the assay of a trace component(s) utilizing a specific antigen-antibody reaction. The basic principles of RIA are as follows. The reaction of a substance labelled or marked with a radioactive isotope (RI) in a given amount and a substance having a specific binding affinity thereto in a given amount results in a coupled product of both of these components, while a part of the labelled substance remains in an unbound or unreacted free state. The reaction proceeds based on the laws of mass action in general, and, therefore, when an unlabelled substance is added to the reaction system, binding with a limited amount of binding protein is decreased and a certain relationship (calibration curve) can be established therebetween. As a result, an amount of an unknown substance can be determined from the calibration curve if the bound substance and the labelled substance in the free state are separated and either one or both are measured with respect to the RI amount.

Due to the high sensitivity and the simplicity of RIA, RIA is particularly applicable to the measurement and inspection of trace amounts of proteins in blood and hormones. Details thereon are given in, e.g., Kumahara and Shizume, *NEW RADIOIMMUNOASSAY*, pages 3 to 10 (1977), published by Asakura Publishing Co., Ltd., Tokyo, *KISO SEIKAGAKU JIKKENHO* (Basic Biochemical Experiments) (6), subtitled "Biochemical Assay" (1967), published by Maruzen Co., Ltd., Tokyo, P. D. Boyer et al, *The Enzyme*, vols. 3, 4 and 5 (1971), published by Academic Press, New York and, *METHODS IN ENZYMOLOGY*, edited by Sidney P. Colowick et al, vols. I, II, III, V and VII, published by Academic Press, New York.

However, RIA is subject to several disadvantages due to the use of RI labelling substances ($^{125}I$, $^{131}I$, etc.) which must have high specific radioactivity to maintain immune activity and must be of high purity. For these reasons, RIA involves the danger of radiation exposure and it is necessary to use expensive and unstable labelling substances which cannot be used for extended periods of time. In addition, special installations, equipment and personnel qualified to deal with radiation are required. Finally, after RIA, disposal of radioactive waste material and the ensuing pollution problems are encountered.

For these reasons, it has been desired to develop a method for the immunological measurement of trace components which is stable and provides sufficient sensitivity without using any isotope.

The inventors have already proposed a method for the measurement of trace components with high sensitivity applicable to immunological measurement using a photographically active substance, e.g., a spectral sensitizer, in combination with silver halide. Such an immunological measurement method previously proposed by the present inventors is basically practiced as follows.

The immunological measurement method comprises:

competitively reacting an antigen or antibody labelled with a spectral sensitizer and an antigen or antibody to be measured with an antibody or antigen which specifically reacts with the respective antigen species or antibody species, bringing either the thus formed reaction product or the unreacted component into contact with a silver halide light sensitive material, exposing the same to light having a wavelength which the spectral sensitizer absorbs, developing the exposed silver, and, quantitatively determining the antigen or antibody based upon the optical density of the resulting silver image and/or the color density obtained.

More specifically, a known amount of a labelled antigen or labelled antibody is reacted with an antigen or antibody. After separating the reaction product and unreacted material, a quantitative assay of the labelling substance (either one) is performed using silver halide to prepare a calibration curve. Based on the calibration curve, an unknown amount of antigen or antibody can be determined. This is because the optical density of the thus formed blackened areas and/or colored dye is proportional to the amount of the spectral sensitizer adsorbed on silver halide, which is in turn proportional to the amount of the antigen or antibody to be measured.

Based upon such a new principle, the present inventors have discovered a basic measurement method for an antigen or antibody as described above (also see U.S. Ser. No. 126,920 filed Mar. 3, 1980 now U.S. Pat. No. 4,337,063, which is hereby incorporated by reference). While this novel photochemical measurement of an antigen or antibody eliminates problems accompanied by RIA and enzyme immunoassay, it is still desired to develop a measurement method having a more improved detection sensitivity in order to obtain results in good reproducibility and high accuracy even in the case where an antigen or antibody to be measured is present in a minute quantity as in the order of μg/ml or less, or even in the case where the immune activity of an antigen or antibody to be measured is very weak.

The present inventors have now discovered that detection sensitivity with silver halide is markedly enhanced when a specific hydrazine compound is present at any stage from bringing the substances labelled with the spectral sensitizer into contact with silver halide to developing silver halide.

SUMMARY OF THE INVENTION

Therefore, an object of this invention is to provide an immunochemical measurement method for an antigen or antibody which provides high sensitivity without using any isotope or enzyme.

Another object of this invention is to provide an immunochemical measurement method which enables one to reduce the quantity of a testing sample (blood, urine, body fluids, etc.) required for improved detection sensitivity and thus enables one to measure multiple test items using the same quantity of a testing sample as used in the prior art.

A further object of this invention is to provide a stabilized reagent employed for the measurement with improved detection sensitivity.

PREFERRED EMBODIMENTS OF THE INVENTION

The hydrazine compound which is employed in accordance with method (I) of this invention is represented by formula (H):

$$R^{1h}-NH-NH-\overset{O}{\underset{\|}{C}}-R^{2h} \qquad (H)$$

$R^{1h}$: an aryl group which may be substituted
$R^{2h}$: a hydrogen atom, an alkyl group which may be substituted or an aryl group which may be substituted.

Further detailed description will be given with respect to the compound represents by formula (H), wherein an alkyl or aliphatic group (including a substituent if any and also including the alkyl moiety present in an alkoxy group, a dialkylamino group, etc.) generally has 1 to 12 carbon atoms in total, preferably 1 to 5 carbon atoms, and an aryl or aromatic group (including a substituent if any and also including the aryl moiety present in an aryloxy group, an aryloxycarbonyl group, etc.) generally has 6 to 18 carbon atoms in total, preferably 6 to 11 carbon atoms, unless otherwise indicated.

The aryl group represented by $R^{1h}$, which may be substituted, is a monocyclic or bicyclic aryl group. Examples are a benzene ring and a naphthalene ring. Particularly preferred ones are those containing a benzene ring.

The aryl group may be substituted. Preferred examples of such substituents are shown below:
(1) Straight, branched and cyclic alkyl groups, preferably containing 1 to 20 carbon atoms, such as a methyl group, an ethyl group, an isopropyl group, an n-dodecyl group, and a cyclohexyl group;
(2) Aralkyl groups, preferably monocyclic and bicyclic aralkyl groups having an alkyl moiety containing 1 to 3 carbon atoms, such as a benzyl group;
(3) Alkoxy groups, preferably containing 1 to 20 carbon atoms, such as a methoxy group and an ethoxy group;
(4) Amino groups, preferably an $-NH_2$ group and those amino groups mono- or di-substituted by an alkyl group containing 1 to 20 carbon atoms, such as a dimethylamino group and a diethylamino group;
(5) Aryloxy groups, preferably a phenoxy group;
(6) Groups represented by $Ah-Xh-(Y)_{nh}-$
(7) groups represented by

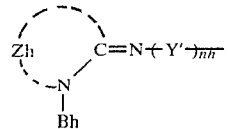

(8) Groups represented by $R^{3h}CONHNH-Ar-Y''-$.

In the formula: $Ah-Xh-(Y)_{nh}-$ as illustrated above, Group (6):
(a) Xh is a divalent linking group selected from the following $x_1$ to $x_{11}$: $x_1 = -CSNH-$, $x_2 = -S-CSNH-$,

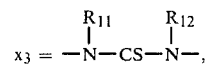

$x_4 = -CONH-$, $x_5 = -O-E-CONH-$,

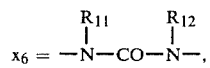

$x_7 = -NHCO-$, $x_8 = -O-$, $x_9 = -SO_2NH-$, $x_{10} = -E-NH-$, and $x_{11} = -E=N-$;
(b) Y is a divalent linking group selected from the following $y_1$ to $y_{11}$: $y_1 = -CONH-$, $y_2 = -E-CONH-$, $y_3 = -E-$, $y_4 = -E-O-E'-$, $y_5 = -E-S-E'-$, $y_6 = -SO_2NH-$, $y_7 = -E-SO_2NH-$, $y_8 = -NHCONH-$, $y_9 = -E-NHCONH-$, $y_{10} = -E-O-E'-CONH'$, and $y_{11} = -E-E'-$,
wherein $R_{11}$ is a hydrogen atom, an aliphatic group (preferably, an alkyl group containing 1 to 20 carbon atoms, a cycloalkyl group containing 3 to 12 carbon atoms, or an alkenyl group containing 2 to 20 carbon atoms), or an aromatic group (preferably, a phenyl group and a naphthyl group),
$R_{12}$ is a hydrogen atom or an aliphatic group represented by $R_{11}$,
$R_{11}$ and $R_{12}$ may combine with each other to form a ring, with preferred examples of such ring being

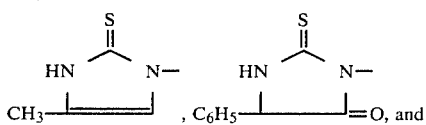

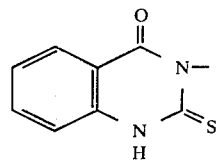

(in this case, Ah represents hydrogen), when $R_{11}$ and $R_{12}$ do not form a ring, any one of $R_{11}$ and $R_{12}$ is a hydrogen atom, and E and E' each represents a saturated or unsaturated divalent aliphatic group (e.g., an alkylene group, such as an ethylene group and a 1-methylpropylene group, and an alkenylene group, such as propenylene group and a butenylene group), a divalent aromatic group (e.g., a phenylene group, a naphthylene group and a 5-amino-1,2-phenylene group), with the exception that in $y_{11} = -E-E'-$, E and E' are divalent groups different from each other and in $x_{11} = -E=N-$, E is $-(CH_2)_{mh}-CH=$ (wherein mh is an integer of 0 to 2);

(c) nh is an integer of 0 or 1, and when nh is 1, particularly preferred combinations of Xh and Y are $x_3$-$y_2$, $x_7$-$y_2$, $x_8$-$y_2$, $x_{12}$-$y_3$, $x_3$-$y_7$, $x_5$-$y_9$, $x_9$-$y_9$, and $x_3$-$y_{10}$; and (d) Ah represents a straight, branched or cyclic alkyl group (preferably containing 1 to 20 carbon atoms, such as a methyl group, a propyl group, and an n-hexyl group), a monocyclic or bicyclic aryl group (e.g., a phenyl group), a monocyclic or bicyclic aralkyl group (preferably containing 7 to 26 carbon atoms, such as a benzyl group), and a heterocyclic radical.

The heterocyclic radical represented by Ah is a 5- or 6-membered ring containing therein at least one hetero atom and may be condensed with an aromatic ring, particularly a benzene ring. Particularly, a heterocyclic radical containing at least one nitrogen atom is preferred. Examples are a thiazolyl group, a benzthiazolyl group, an imidazolyl group, a thiazolinyl group, a pyridinyl group, a tetrazolyl group, a benztriazolyl group, an indazolyl group, a benzimidazolyl group, a hydroxytetrazainden-2 or 3-yl group; mercapto group-containing heterocyclic groups, such as 2-mercaptobenzthiazolyl group and a 2-mercaptobenzoxazolyl group; and quaternary nitrogen atom-containing heterocyclic radicals, such as 2-methylbenzthiazolinium-3-yl, 2-(N-sulfoethylbenzthiazolinio), and N,N-dimethylbenzimidazolinium-2-yl.

The foregoing groups represented by Ah may be substituted. Examples of such substituents include:
- an alkoxy group (preferably containing 1 to 18 carbon atoms, such as a methoxy group),
- an alkoxycarbonyl group (preferably containing 2 to 19 carbon atoms, such as an ethoxycarbonyl group),
- a monocyclic or bicyclic aryl group (e.g., a phenyl group),
- an alkyl group (preferably containing 1 to 20 carbon atoms, such as a methyl group and a tert-amyl group),
- a dialkylamino group (preferably containing 1 to 20 carbon atoms, such as a dimethylamino group),
- an alkylthio group (preferably containing 1 to 20 carbon atoms, such as a methylthio group),
- a mercapto group, a hydroxy group, a halogen atom, a carboxy group, a nitro group, a cyano group,
- a sulfonyl group (preferably containing 1 to 20 carbon atoms, such as a methylsulfonyl group), and
- a carbamoyl group (preferably containing 1 to 20 carbon atoms, such as a carbamoyl group and a dimethylcarbamoyl group).

In the foregoing group represented by Group (7)

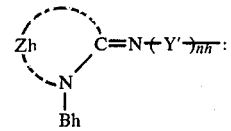

(a) Zh is a group of non-metallic atoms and combines with

to form a 5- or 6-membered heterocyclic ring, with suitable examples of such 5- or 6-membered heterocyclic rings being a thiazoline ring, a benzthiazoline ring, a naphthothiazoline ring, a thiazolidine ring, an oxazoline ring, a benzoxazoline ring, an oxazolidine ring, a selenazoline ring, a benzselenazoline ring, an imidazoline ring, a benzimidazoline ring, a tetrazoline ring, a triazoline ring, a thiadiazoline ring, a 1,2-dihydropyridine ring, a 1,2-dihydroquinone ring, a 1,2,3,4-tetrahydroquinoline ring, a perhydro-1,3-oxazine ring, a 2,4-benz[d]oxazine ring, a perhydro-1,3-thiazine ring, a 2,4-benz[d]thiazine ring and a uracyl ring;

(b) Bh is a hydrogen atom or a saturated or unsaturated aliphatic group [such as an alkyl group (preferably containing 1 to 20 carbon atoms, e.g., a methyl group and an ethyl group), an alkenyl group (preferably containing 2 to 22 carbon atoms, e.g., an allyl group), and an alkynyl group (preferably containing 2 to 20 carbon atoms, e.g., a butynyl group)], which may be substituted by an alkoxy group, an alkylthio group, an acylamino group, an acyloxy group, a mercapto group, a sulfo group, a carboxy group, a hydroxy group, a halogen atom, an amino group, or the like;

(c) Y' has the same meanings as described for Y in Group (6); and (d) nh is 0 or 1.

In the group represented by the formula: $R^{3h}CONHNH-Ar-Y''-$, Group (8):

(a) $R^{3h}$ is the same as $R^{2h}$ as described hereinafter;

(b) $-Ar-$ represents a divalent aryl group, preferably a phenylene group, which may be substituted; and (c) Y'' is the same as Y described in Group (6), with divalent linking groups represented by $y_3$ to $y_5$ being particularly preferred.

In formula (H), $R^{2h}$ is a hydrogen atom, an alkyl group which may be substituted, or an aryl group which may be substituted. Substituents which can be used include a halogen atom, a cyano group, a carboxy group, and a sulfo group. Examples of such alkyl and aryl groups are a methyl group, an ethyl group, an n-propyl group, an isopropyl group, a phenyl group, a 4-chlorophenyl group, a 4-bromophenyl group, a 3-chlorophenyl group, a 4-cyanophenyl group, a 4-carboxyphenyl group, a 4-sulfophenyl group, a 3,5-dichlorophenyl group, and a 2,5-dichlorophenyl group.

Of the substituents represented by $R^{2h}$, a hydrogen atom, a methyl group and a phenyl group (including a substituted phenyl group) are preferred, and a hydrogen atom is particularly preferred.

Preferred examples of the compounds represented by formula (H) are described in U.S. Pat. Nos. 4,168,977 and 4,224,401 and British Pat. No. 1,558,946, Japanese Patent Application (OPI) Nos. 52050/80 and 90940/80, *Research Disclosure*, No. 17626 (Vol. 176, 1978), etc. Of these compounds, those described in U.S. Pat. Nos. 4,168,977 and 4,224,401 are particularly preferred.

Specific examples of compounds represented by formula (H) are shown below, but this invention is not limited only thereto.

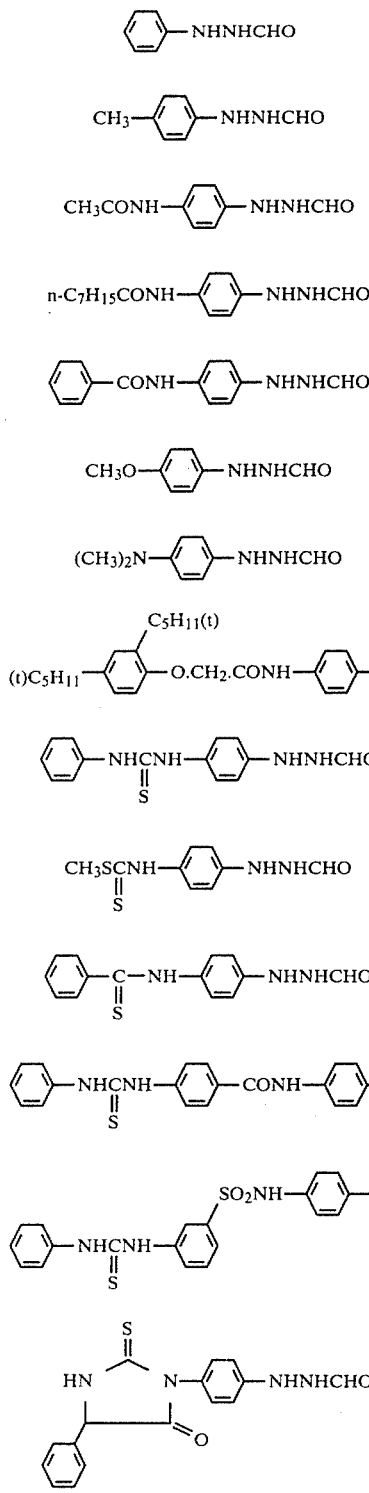

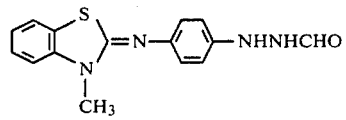
Compound H-15

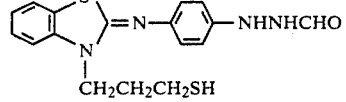
Compound H-16

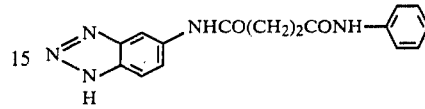
Compound H-17

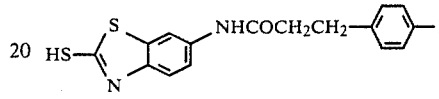
Compound H-18

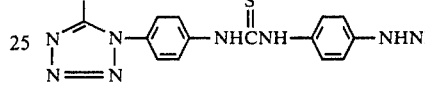
Compound H-19

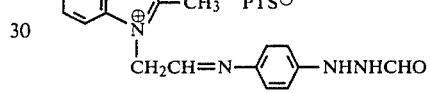
Compound H-20

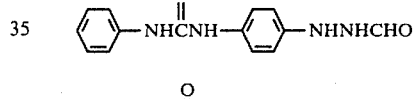
Compound H-21

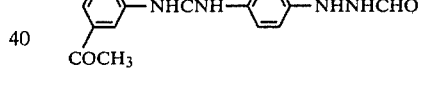
Compound H-22

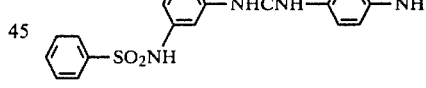
Compound H-23

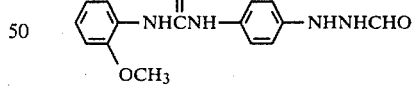
Compound H-24

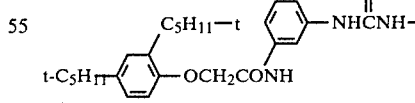
Compound H-25

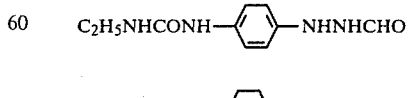
Compound H-26

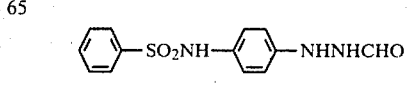
Compound H-27

Compound H-28

-continued

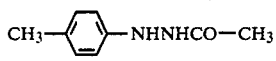 Compound H-29

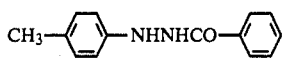 Compound H-30

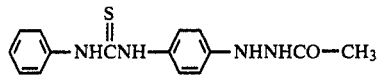 Compound H-31

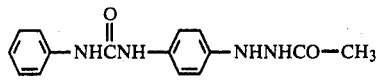 Compound H-32

These compounds can be synthesized by methods as described in U.S. Pat. Nos. 4,168,977 and 4,224,401, and British Pat. No. 1,558,946, Japanese Pat. applications OPI Nos. 20921/78, 20922/78, 66732/78 and 20318/78, all of which are incorporated herein by reference.

In order to bring the spectral sensitizer labelling substance into contact with silver halide or to absorb the spectral sensitizer to silver halide, exposing or developing, in the state where the hydrazine compound is present, the hydrazine compound can be present in a testing sample, can be previously incorporated into the silver halide light sensitive material or can be added to a developer, etc.

The amount of the compound represented by formula (H) is generally in the range of from $10^{-8}$ to $10^{-1}$ mol/mol Ag, preferably $10^{-6}$ to $10^{-2}$ mol/mol Ag, when the hydrazine compound is incorporated into the silver halide light sensitive material.

To incorporate the compound represented by formula (H) into the light sensitive material, methods as are conventionally used for adding additives to photographic emulsions are applicable. For example, the hydrazine compound can be added to photographic emulsions or light insensitive hydrophilic colloid solutions in the form of an aqueous solution of a suitable concentration when the compound is soluble in water, it can be added in the form of a solution obtained by dissolving the hydrazine compound in an appropriate solvent compatible with water which does not adversely affect photographic properties, e.g., selected from alcohols, glycols, ketones, esters, amides, etc. Techniques used for adding water insoluble (oil soluble) couplers to emulsions as a dispersion thereof, which are well known in the photographic art, also apply to this invention.

In the case that the hydrazine compound shown by formula (H) is incorporated into a photographic prebath or developer or a buffer solution employed for the immune reaction, the amount thereof is generally in the range of from 5 mg. to 15 g., preferably 10 mg. to 5 g., per 1 liter of the pre-bath, developer or buffer solution.

The most preferred technique in this invention is that where the hydrazine compound is mixed with the silver halide emulsion and the mixture is coated to form an analysis element.

In order to minimize an undesired blank density in method (I) of this invention, anti-foggants which are conventionally used for photographic emulsions can also be added to a testing sample, a spot solution, the silver halide light sensitive material or a developer.

The spectral sensitizer for photographic use employed for the sensitizer-labelled substance utilized in this invention, for labelling a trace component such as an antigen or antibody possesses the capability to impart spectral sensitization to silver halide. Such spectral sensitizers are known as spectral sensitizers for photographic light sensitive materials and include, e.g., cyanine dyes, merocyanine dyes, hemicyanine dyes, styryl dyes, etc. These dyes are specifically described in The Theory of the Photographic Process (4th edition), edited by T. H. James (1977), published by Macmillan Co., Ltd., *Cyanine Dyes and Related Compounds*, F. M. Hamer (1964), Interscience Publishers, etc.

In more detail, merocyanine dyes as described in U.S. Pat. Nos. 2,493,748, 2,519,001 and 2,652,330, German Pat. No. 1,177,481 and French Pat. No. 1,412,702, cyanine dyes as described in U.S. Pat. Nos. 2,238,213, 2,503,776, 2,537,880, 3,196,017 and 3,397,060, German Pat. Nos. 929,080, 1,028,718, 1,113,873, 1,163,671 and 1,177,482, French Pat. No. 1,359,683, British Pat. Nos. 840,223, 886,270, 886,271 and 904,332, Belgian Pat. No. 654,816 and Japanese patent publications Nos. 14112/65 and 23467/65 ("patent publication" used in the specification means an application published for purpose of opposition and is available for public inspection), etc., are all effective dyes for this invention.

These dyes can also be employed in combinations of two or more thereof. For example, supersensitization including the use of dyes as described in Japanese patent publications Nos. 4932/68, 4936/68, 22884/68, etc. is also effective for this invention. Further, supersensitization as described in U.S. Pat. Nos. 2,947,630, 2,933,390, 2,937,089, 3,617,295 and 3,635,721, French Pat. No. 1,500,218, etc., is also effective. In this case, the supersensitizing dye combination can be mixed together with the labelled trace components, such as an antigen or antibody, or can be previously incorporated into the silver halide emulsion.

Of these spectral sensitizers, the dyes described below are particularly advantageous as the labelling substance(s) since these dyes are excellent in binding to the trace components such as an antigen or antibody. In this invention, such spectral sensitizers as having an absorption region at a longer wavelength (preferably longer than 500 nm) than the absorption wavelength region intrinsic to silver halide, which spectrally sensitize silver halide grains by contact with (adsorption to) the silver halide grains, are employed.

Preferred spectral sensitizers are described by reference to formulae (C), (M), (R), (M') and (C') below, wherein, unless otherwise indicated, an alkyl group (including a substituent, if any, and also including the alkyl moiety present in an alkoxy group, a dialkylamino group, etc.) generally possesses 1 to 12 carbon atoms, preferably 1 to 5 carbon atoms in total and an aryl group (including a substituent, if any, and also including the aryl moiety present in an aryloxy group, a diarylamino group, etc.) generally possesses 6 to 18 carbon atoms, preferably 6 to 11 carbon atoms.

(1) Cyanine dyes of formula (C) below containing at least one of a mercapto group, an amino group, a hydroxy group or a carboxy group in the heterocyclic nucleus thereof:

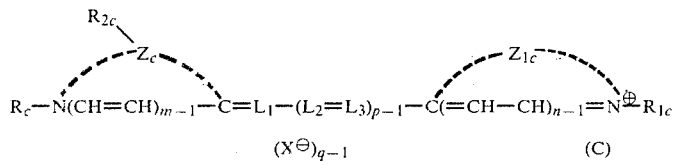

$$(X^{\ominus})_{q-1} \quad (C)$$

wherein m and n each represents 1 or 2; p represents 2 or 3; q represents 1 or 2' $L_1$, $L_2$ and $L_3$, which may be the same or different, each represents a methine group (which may be substituted with an alkyl group, a halogen atom, an aryl group, etc.); $Z_c$ and $Z_{1c}$ each represents a non-metallic atomic group necessary for completing a 5- or 6-membered nitrogen-containing heterocyclic nucleus, which may be the same or different; $R_c$ and $R_{1c}$, which may be the same or different, each represents a substituted or unsubstituted alcohol residue, $R_{2c}$ is a substituent for $Z_c$ and represents a hydrogen atom or $-P_i-Q_j-W_c$ which will be later explained in detail; and X represents an inorganic or organic anion.

Examples of the heterocyclic nuclei formed together with $Z_c$ or $Z_{1c}$ include a thiazole nucleus, a benzothiazole nucleus, a naphthothiazole nucleus, a thiazoline nucleus, an oxazole nucleus, an oxazole nucleus, a benzoxazole nucleus, a naphthoxazole nucleus, an oxazoline nucleus, a selenazole nucleus, a benzoselenazole nucleus, a naphthoselenazole nucleus, a 3,3-dialkylindolenine nucleus, an imidazole nucleus, a pyridine nucleus (e.g., 2-pyridine, 4-pyridine, 5-methyl-2-pyridine, 3-methyl-4-pyridine, etc.), a quinoline nucleus, an imidazo[4,5-d]quinoxaline nucleus, an oxadiazole nucleus, a thiadiazole nucleus, a tetrazole nucleus, a pyrimidine nucleus, etc.

In the definitions above for $L_1$ through $L_3$ and $Z_c$ and $Z_{1c}$, preferred examples of the alkyl group appearing therein include an alkyl group, particularly having 1 to 8 carbon atoms, such as an unsubstituted alkyl group (e.g., methyl, ethyl, propyl, isopropyl, butyl, etc.) or a hydroxyalkyl group (e.g., 2-hydroxyethyl, 3-hydroxypropyl, etc.); and preferred examples of the aryl group include phenyl, alkyl (e.g., methyl)-substituted phenyl, alkoxy (e.g., methoxy)-substituted phenyl, etc.

Prefered examples of the inorganic or organic anions represented by X include chloride, bromide, iodide, p-toluenesulfonate, p-nitrobenzenesulfonate, methanesulfonate, methylsulfate, ethylsulfate, perchlorate, etc.

Preferred examples of the alcohol residues represented by $R_c$ and $R_{1c}$ are an alkyl group having 1 to 18 carbon atoms, preferably having 1 to 7 carbon atoms, such as an unsubstituted alkyl group, a substituted alkyl group with, e.g., an aralkyl group, a hydroxyalkyl group, an alkyl group substituted with a sulfo group, a carboxyalkyl group, a sulfatoalkyl group, a heterocyclic ring-substituted alkyl group), or an aryl group.

When q is 1, the dye forms a betaine type structure.

In the moiety $-P_i-Q_j-W_c$ for $R_{2c}$, wherein P represents

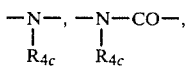

—CO—, —O— or —S— [wherein $R_{4c}$ represents a hydrogen atom, an alkyl group having 1 to 8 carbon atoms, a substituted alkyl group; Q represents an alkylene group having 1 to 10 carbon atoms, a substituted alkylene group (i.e., $$-\overset{|}{\underset{R_{5c}}{C}}H-$$

wherein $R_{5c}$ is methyl, ethyl, propyl, isopropyl, isobutyl, t-butyl, hydroxymethyl, 1-hydroxyethyl, mercaptomethyl, 2-methylthioethyl, benzyl, 3-indolylmethyl, etc.), an arylene group (e.g., phenylene), a substituted arylene group (e.g., substituted phenylene), an aralkylene group, an alkarylene group or a dipeptide or tripeptide residue; i and j each represents 0 or 1, which may be the same or different; and $W_c$ represents a mercapto group, an amino group, a hydroxy group or a carboxy group.

In formula (C) above, at least one of $R_c$, $R_{1c}$, $R_{2c}$ and $Z_{1c}$ contains at least one group selected from the class consisting of a mercapto group, an amino group, a hydroxy group and a carboxy group.

(2) Merocyanine dyes of formula (M) below, containing at least one of a mercapto group, an amino group, a hydroxy group and a carboxy group:

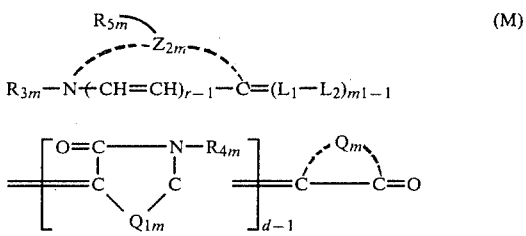

wherein
$Z_{2m}$ has the same meaning as $Z_c$ and $Z_{1c}$;
$R_{3m}$ and $R_{4m}$ have the same meanings as $R_c$ and $R_{1c}$;
$R_{5m}$ has the same meaning as $R_{2c}$; r has the same meaning as n; $L_1$ and $L_2$ are as defined above:
$m_1$ represents 2, 3 or 4;
d represents 1, 2 or 3;
$Q_{1m}$ represents an oxygen atom, a sulfur atom or $-N-R_{6m}$ ($R_{6m}$ represents an aliphatic group);
$Q_m$ represents a non-metallic atomic group necessary for completing a 5-membered or 6-membered nitrogen-containing heterocyclic nucleus; examples of such heterocyclic nuclei include a 2-pyrazolin-5-one nucleus (e.g., 3-methyl-1-phenyl-2-pyrazolin-5-one nucleus, etc.), an isoxazole nucleus, an oxyindole nucleus, a barbituric acid nucleus or 2-thiobarbituric acid nucleus, a rhodanine nucleus (e.g., rhodanine nucleus, 3-sulfoalkyl-rhodanine nuclei, 3-sulfoaryl-rhodanine nuclei, 3-alkyl-rhodanine nuclei, etc.), a 2,4-thiazolidinone nucleus, a thiazolidinone nucleus, a 2,4-imidazolidinedione (hydantoin)nucleus, a 2-thio-2,4-imidazolidinedione nucleus, etc.

In formula (M), at least one of $R_{3m}$, $R_{4m}$, $R_{5m}$, $Q_{1m}$ and $Q_m$ contains at least one group selected from the class consisting of a mercapto group, an amino group, a hydroxy group and a carboxy group.

(3) Rhodacyanine dyes shown by formula (R) below, containing at least one of a mercapto group, an amino group, a hydroxy group and a carboxy group:

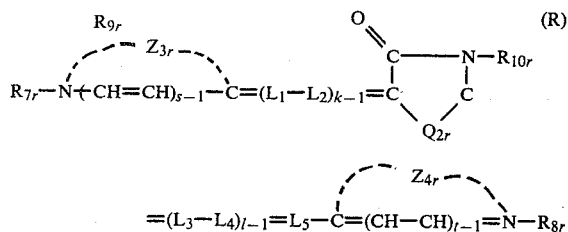

wherein $Z_{3r}$ and $Z_{4r}$ have the same meanings as $Z_c$ and $Z_{1c}$;

$R_{7r}$ and $R_{8r}$ have the same meanings as $R_c$ and $R_{1c}$;

$R_{9r}$ is the same as $R_{2c}$; s and t are the same as m and n;

$L_1$ and $L_5$ are the same as $L_1$ to $L_3$;

$R_{10r}$ is the same as $R_{4m}$; $Q_{2r}$ is the same as $Q_{1m}$;

k and l represent 1, 2 or 3, and may be the same or different.

At least one of $R_{7r}$, $R_{8r}$, $R_{9r}$, $R_{10r}$ and $Q_{2r}$ contains at least one group selected from the class consisting of a mercapto group, an amino group, a hydroxy group and a carboxy group.

Of spectral sensitizers (1) to (3) described above, merocyanine dyes shown by formula (M′) below, containing a carboxy group on the acidic nucleus and cyanine dyes shown by formula (C′) hereafter are particularly preferred.

(4) Preferred merocyanine dyes:

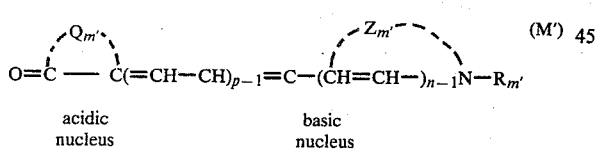

wherein n represents 1 or 2; p represents 2 or 3; $Z_{m'}$ represents a non-metallic atom group necessary for completing a 5- or 6-membered nitrogen-containing heterocyclic nucleus; $R_{m'}$ represents an alcohol residue; and $Q_{m'}$ represents a non-metallic atom group necessary for completing a 5- or 6-membered nitrogen-containing heterocyclic nucleus, wherein the hetero atom is selected from representative nitrogen, sulfur, selenium and oxygen, one of which is connected to a substituent containing a carboxy group: $-P_i-Q_j-$ COOH wherein P, Q, i and j are the same as defined above, directly or via an alkylene, substituted alkylene, arylene, substituted arylene, aralkylene or alkarylene group.

Preferred examples of the heterocyclic nuclei formed by $Q_{m'}$ include a thiazole nucleus, a benzothiazole nucleus (e.g., 6-nitrobenzothiazole, 4-methylbenzothiazole, etc.), a naphthothiazole nucleus, a thiazoline nucleus, an oxazole nucleus, a benzoxazole nucleus, a naphthoxazole nucleus, an oxazoline nucleus, a selenazole nucleus, a benzoselenazole nucleus, a naphthoselenazole nucleus, a 3,3-dialkylindolenine nucleus, an imidazole nucleus, a pyridine nucleus (e.g, 2-pyridine, 4-pyridine, 5-methyl-2-pyridine, 3-methyl-4-pyridine, etc.), a quinoline nucleus, an imidazo[4,5-d]quinoxaline nucleus, an oxadiazole nucleus, a thiadiazole nucleus, a tetrazole nucleus, a pyrimidine nucleus, etc.

Preferred examples of the alcohol residues shown by $R_{m'}$ are an alkyl group having 1 to 18 carbon atoms, preferably having 1 to 7 carbon atoms, such as an unsubstituted alkyl group, a substituted alkyl group having a substituent (e.g., an aralkyl group, a hydroxyalkyl group, a sulfo-substituted alkyl group, a carboxyalkyl group, a sulfato-alkyl group, a heterocyclic ring-substituted alkyl group, etc.), or an aryl group.

Unless otherwise indicated above, the definitions of the symbols and preferred examples thereof are the same as those for formula (M).

(5) Preferred cyanine dyes:

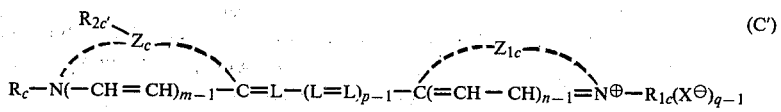

wherein m, n, p, q, $Z_c$, $Z_{1c}$, X, $R_c$ and $R_{1c}$ are as defined in formula (C) above;

L represents a methine group (which may be substituted with an alkyl group, e.g., methyl, ethyl, etc., an aryl group, e.g., phenyl, etc., a halogen atom, e.g., chlorine, bromine, etc.); further preferred examples of the alkyl group as a substituent for the methine group L include an alkyl group having 1 to 8 carbon atoms (e.g., methyl, ethyl, propyl, isopropyl, butyl), a hydroxyalkyl group (e.g., 2-hydroxyalkyl, 3-hydroxypropyl, etc.) or the like and for the aryl group, phenyl, halogen (e.g., chlorine)-substituted phenyl, alkyl (e.g., methyl)-substituted phenyl, alkoxy (e.g., methoxy)substituted phenyl, etc.).

$R_{2c'}$ is a substituent for $Z_c$ and represented by formula:

$$-P_i-Q_j-COOH$$

wherein P, Q, i and j are as defined hereinbefore.

The merocyanine dyes and cyanine dyes shown by formulae (M′) and (C′), respectively, are excellent as labelling substances for this invention, for example, in solubility, reaction yield, etc.

Labelling of an antigen or antibody with the spectral sensitizer for photographic use is effected through a chemical reaction. That is, the spectral sensitizer is introduced into the antigen or antibody via a covalent bond, thus forming a labelled antigen or labelled antibody. It is preferred that the spectral sensitizer and the antigen or antibody contain an amino group, an imino group, a mercapto group, a carboxy group, a carboxylic acid amido group or a hydroxy group and a group capable of directly reacting with such a group as a functional group which takes part in the immune reaction. In both the labelling substance and the antigen or antibody, such a functional group may previously be present in the molecule thereof, or may be introduced through a chemical reaction.

Linking between these functional groups (i.e., one functional group present on an antigen or antibody plus one functional group present on a spectral sensitizer)

may be formed directly therebetween or formed through a suitable linking group ③. Compounds which provide linking group ③ preferably contain the same functional groups as those for the antigen or antibody or may contain groups other than these functional groups which can react directly with these functional groups. Further, compounds which provide linking group ③ may also contain an amino acid, peptide, polyamino acid, nucleoside, nucleotide, polynucleoside, polynucleotide moiety, etc. A method of forming the linking between these functional groups can be any of the following:

(1) Spectral sensitizers are directly reacted with the aforesaid functional groups;
(2) Spectral sensitizers and the aforesaid functional groups are reacted using an activating agent, and
(3) Spectral sensitizers and the aforesaid functional groups are reacted through at least one compound having a bifunctional group.

Groups which are reactive with the aforesaid functional groups of antigens or antibodies and methods for reacting the same are described in detail, in, e.g., *Lectures on Experimental Biochemistry*, vol. 1 subtitled "Chemistry of Proteins," ibid., vol. 2, subtitled "Chemistry of Nucleic Acids," ibid., vol. 3 subtitled "Chemistry of Lipids" and ibid., vol. 4, subtitled "Chemistry of Sugars," all edited by the Biochemical Association, Japan, published by Tokyo Kagaku Dojin (1977); Izumiya, *PEPTIDE GOSEI* (Peptide Synthesis), Greenstein et al. *CHEMISTRY OF THE AMINO ACIDS*, vols. I-III (1961), John-Wiley & Sons Inc., New York. One skilled in the art can easily perform such reactions for forming the linking from knowledge in the art and these publications.

Examples of compounds containing groups which react with the aforesaid functional groups further include, e.g., activated esters, activated halogens, aldehydes, activated vinyl esters, activated halogens, aldehydes, activated vinyl compounds, acid anhydrides, acid halides, thioisocyanates, isocyanates, carboxylic acids, amides, alkyl halides, nitrophenyl halides, etc. Accordingly, these functional groups can originally be present in the spectral sensitizer or can be introduced as a result of the reaction of a compound having a bifunctional group and the spectral sensitizer.

Reaction conditions for labelling vary depending upon the kind of the antigen or antibody, the kind of spectral sensitizer, etc., and conditions are selected so as to not damage the biological activity of the antigen or antibody to be labelled. Accordingly, the reaction temperature is generally chosen from the range of from 40° to 60° C., preferably −20° to 40° C.; and the reaction time from the range of from 10 mins. to 16 hrs. The reaction pressure is preferably atmospheric pressure, but can suitably chosen from the range of 1 to 20 atms. It is advantageous that water or a pH buffer solution be used as a solvent for the labelling. Organic solvents such as DMF (dimethylformamide), methylene chloride, etc. can also be employed. These reaction conditions are common to reaction conditions which are generally applicable to modification of proteins or enzymes and details are described in the publications referred to above.

The amount of spectral sensitizer used for labelling varies depending upon the kind of the aforesaid substances to be labelled, but is generally in a molar ratio of 1/100 to 100 moles per 1 mole of the antigen or antibody, preferably 1/20 to 20 times, more preferably ½ to 2 times, same basis.

As methods for confirming completion of labelling, methods for measuring spectra such as UV, visible rays, IR, mass and NMR spectra, etc., and a method confirming labelling via disappearance of the terminal group at which the labelling substance is to be introduced, are representative. Simple tests will be enough to confirm completion of labelling. Where it is confirmed utilizing absorption spectrum, following completion of the labelling reaction, an absorption spectrum of a separated and purified product is measured; if the resulting absorption spectrum is consistent with the intrinsic absorption spectrum which a spectral sensitizer possesses, it is confirmed that the labelling reaction was effected. A further method for confirming the labelling being effected is to analyze the presence or absence of the specific terminal groups, e.g., an amino or carboxy group(s). In case that the spectral sensitizer is introduced at the terminal amino group(s) of the spectral sensitizer, it is confirmed by the analysis of the N-terminal that completion of the labelling reaction has been effected if the corresponding amino acid(s) to an amino group(s) on which labelling is to occur are not detectable. Detailed disclosure on such N terminal analysis is described in, e.g., B. S. Hartley and V. Massey, *Biochim. Biophys. Acta*, 21, 58 (1956) (generally referred to as a Dansyl method in the art), *Archn. Biochem. Biophys.*, 22, 475 (1949) (a PTC (phenol isocyanate) method), F. Sanger, *Biochem. J.*, 39, 507 (1945) (a dinitrofluorobenzene method), etc. In a similar manner, the terminal carboxy group(s) are analyzed to check completion of the labelling reaction, details of which are given in, e.g., S. Akabori, K. Ohno and K. Narita, *Bull. Chem. Soc. Japan*, 25, 214 (1952) (generally referred to as a hydrazine decomposition method in the art), H. Matuo, U. Fujimoto and T. Tatuno, *Biochem. Biophys. Res. Comminication*, 22, 69 (1966) (a tritium marking method), etc. Further, details of these terminal determination methods are also given as a review in S. B. Needleman, *PROTEIN SEQUENCE DETERMINATION*, published by Springer Verlag (Berlin), 1975.

According to the aforesaid spectral methods, after the labelling reaction is completed, the reaction product is separated and purified; thereafter the spectrum inherent to the labelled reaction product is measured to confirm the completion of labelling. For example, visible absorption spectrum is measured, and if the spectrum is identical with the inherent absorption spectrum of the spectral sensitizer used for the labelling in the visible region, taking into account solvation, association, etc., completion of the labelling is confirmed. As is described above, if the labelling is effected the terminal amino group or carboxy group of the trace component is not detected upon analysis for the terminal group, and the effected labelling is thereby confirmed.

To separate the labelled antigen-antibody reaction product (B) from the labelled free antigen or antibody (F) in method (I) of this invention, various separation techniques conventionally used in the art are employed. Typical examples include liquid chromatography techniques (e.g., gel filtration, ion exchange, partition chromatography, adsorption chromatography including affinity chromatography, microfilter filtration, dialysis, adsorption using cellulose, talc, dextran powder, etc., salting out (separation of precipitated and aggregated matters formed by adding a salt to a system, see, L. Wide and C. A. Gemzell, *Ciba Foundation Colloq. on*

*Endocrinol.*, 14, 296 (1962)), a precipitation (separation of crystallized specific protein formed due to difference of dielectric point, etc., which occurs by changing pH, see, G. M. Brodsky and P. H. Forsham, *J. Clin. Invest.*, 39, 1070 (1960)), centrifugation, crystallization, extraction, solid phase separation, etc., can be used. Detailed disclosure of these separation techniques is provided in Kazuo Shizume and Yuichi Kumahara, *NEW RADIO-IMMUNOASSAY*, 1967, published by Asakura Publishing Co., Ltd., Tokyo, *DATA OF BIOCHEMISTRY*, second separate volume, Chapter 10, edited by the Biochemical Association, Japan, published by Tokyo Kagaku Dojin, 1980, etc.

A further preferred embodiment in practicing this invention is to provide a water absorbing layer in an analysis element used for the measurement method of this invention. The provision of such a water absorbing layer is of importance in increasing the amount of a testing sample spotted onto the analysis element. The water absorbing layer functions to accelerate absorption of the spotted testing sample into the analysis element to thereby increase uptake of the compound to be measured in the testing sample into a light sensitive layer, and, as a result, increases the amount of the compound to be adsorbed to silver halide.

By the provision of a water-absorbing layer, the immune reaction proceeds to obtain a good quantitative response between the reaction product and unreacted component so that detection sensitivity and reproducibility, as well as accuracy are all improved.

The water absorbing layer essentially increases the amount of "water" absorbed.

The term "water" used herein with reference to the water absorbing layer refers to a testing sample containing a compound to be measured (i.e., analyte) which is an aqueous solution of the analyte.

The water absorbing layer is essentially insensitive to light and preferably is swellable upon contact with water.

It is preferred that the water absorbing layer used in the analysis element be composed of, e.g., a porous membrane, a filter paper, a fiber, etc., or a binder comprising gelatin and/or a polymer and it is preferred that the water absorbing layer be easily set (gelled) by cold air after coating. From this viewpoint, it is preferred to use at least 50 wt% of gelatin based on the total weight of binder when a mixture of gelatin and a polymer is used as the binder. To further increase the water absorption rate of the water absorbing layer, other polymers can also be effectively employed.

It is preferred that the water absorbing layer of this invention have a thickness of from 1 to 100μ, preferably about 5 to about 40μ.

The water absorbing layer can also contain, in addition to gelatin or polymers, silver halide and additives for conventional silver halide light sensitive materials, e.g., an antifogging agent, a dye, a surface active agent, colloidal silver and the like.

As gelatin employed for the water absorbing layer, conventional lime-treated gelatin, acid-treated gelatin, enzyme-treated gelatin obtained by treating lime- or acid-treated gelatin further with an enzyme, gelatin derivatives obtained by further treating these gelatins chemically, e.g., phthalated gelatin; grafted gelatin obtained by graft-polymerizing a monomer on such gelatins, etc., can be employed singly or in combination by mixing them in optional proportions.

It is preferred that polymers used in this invention be liable to swell or dissolve in water examples of which are materials obtained by chemically modifying gelatin, such as phthalated gelatin, or graft gelatin obtained by graft polymerizing a monomer in the presence of gelatin. Such gelatin may be used alone or as a mixture thereof in an appropriate proportion. As polymers used in this invention, polymers which are liable to swell or dissolve in water are preferred, examples of which include albumin, agar agar, gum aragic, alginic acid, a hydrophilic homopolymer or copolymer of a polymerizable vinyl monomer such as vinyl, alcohol, vinyl pyrrolidone, acrylamide, acrylic acid, methacrylic acid, styrenesulfonic acid, styrene, methyl methacrylate, etc., a cellulose compound (e.g., hydroxyethyl cellulose, carboxymethyl cellulose, dextran, etc.), water soluble starch, etc. If necessary or desired, a hardening agent can also be added thereto render the same less soluble.

The components labelled with spectral sensitizer which are employed for the immunochemical measurement in accordance with this invention are generally dissolved in an aqueous medium and an immune reaction is caused in the resulting aqueous solution. The present inventors have noted that it is very important to stabilize the labelled components in an aqueous medium to achieve high sensitivity and high reproducibility, and this is attained by the use of a specific compound of formula (S) described below, singly or in combination with the hydrazine compound of formula (H), in the photochemical measurement system of this invention.

The compound of formula (S) stabilizes the components labelled with spectral sensitizers, which participate in the above reaction, in an aqueous medium and provides extremely improved detection sensitivity.

This invention is thus also directed to a reagent suitable for the immunochemical measurement of a trace component(s) which comprises a trace component labelled with a spectral sensitizer and a compound represented by formula (S) below in a water containing solvent (aqueous medium) and to a method for immunochemically assaying a trace component(s) using the reagent having improved stability.

The compound used for stabilization of the dye labelled substances is represented by formula (S) below.

$$D_1-A-D_2 \qquad (S)$$

wherein $D_1$ and $D_2$ each represents a condensed polycyclic aromatic heterocyclic moiety or an aromatic heterocyclic ring-substituted amino group, which may contain an $-SO_3M$ group, wherein M is a hydrogen atom, an alkali metal or ammonium group, provided that the $-A-$ moiety should contain an $-SO_3M$ group when no $-SO_3M$ group is contained in either $D_1$ or $D_2$ described above.

In formula (S), examples of the condensed polycyclic aromatic heterocyclic residue represented by $D_1$ and $D_2$ include a 2-benzotriazolyl group, a 2-naphthotriazolyl group, etc.; and examples of the aromatic heterocyclic ring-substituted amino group include a 1,3,5-triazin-2-yl amino group, a 1,3-diamin-2-yl amino group, etc.

Preferred examples of the divalent aromatic groups represented by A are as follows:
Sulfo-Containing Groups:

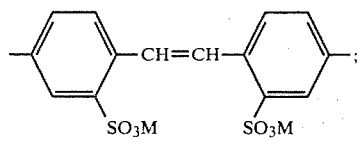
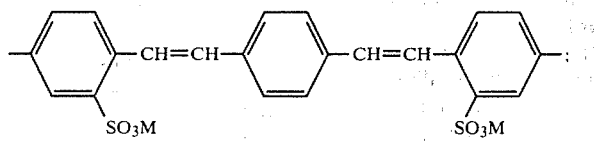
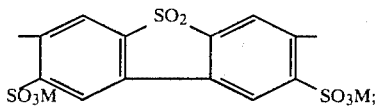
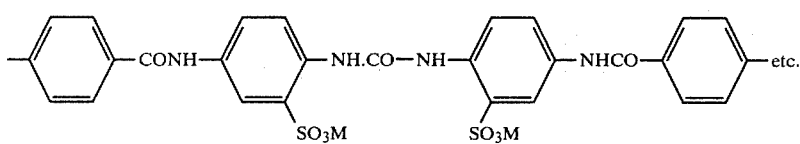
Groups free of a sulfo group:
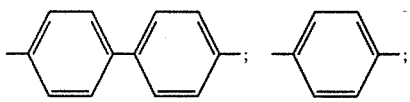
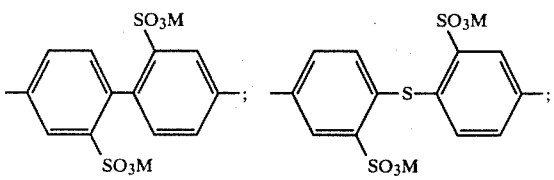
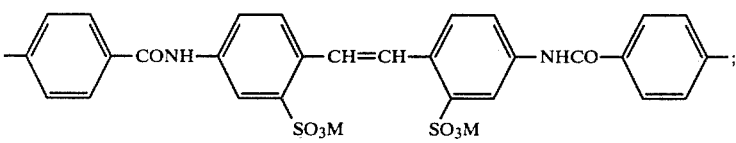
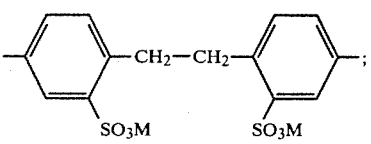
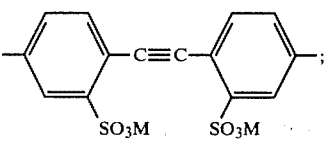
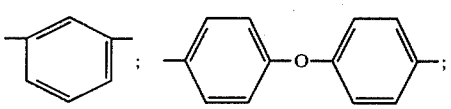

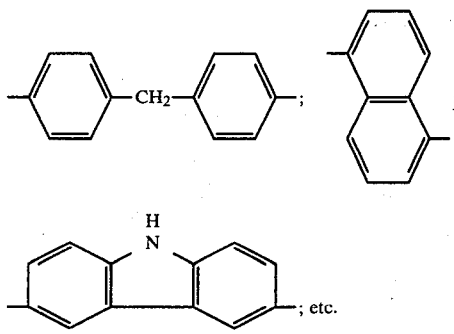

When no sulfo group is contained in A, at least one of $D_1$ and $D_2$ contains an —$SO_3M$-containing group.

Of these divalent aromatic residues, more preferred is:

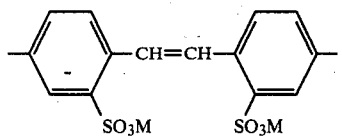

Examples of the alkali metal represented by M include sodium, potassium, etc., and examples of the halogen atom include chlorine, bromine, iodine, etc.

Of compounds represented by formula (S), particularly preferred are those represented by the following formulae (S-I) and (S-II), wherein an alkyl group (including the alkyl moiety contained in an alkoxy group, an alkylthio group, etc. and including a substituent thereon, if any) generally has 1 to 20 carbon atoms, preferably 1 to 12 carbon atoms and an aryl group (including the aryl moiety contain in an aryloxy group, an arylthio group, etc. and including a substituent thereon, if any) generally has 6 to 30 carbon atoms, preferably 6 to 15 carbon atoms, unless otherwise indicated.

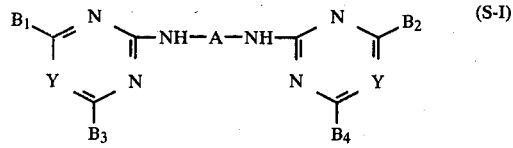

wherein —A— has the same meaning as in formula (S); Y represents =CH—, =$CB_5$— or =N— wherein $B_5$ represents a lower alkyl group, a halogen atom, etc.; $B_1$, $B_2$, $B_3$ and $B_4$ each represents a hydrogen atom, a hydroxy group, an alkoxy group, a lower alkyl group (e.g., a methyl group, an ethyl group, etc.), an aryloxy group (e.g., a phenoxy group, an o-tolyloxy group, a p-sulfophenoxy group), a halogen atom (e.g., a chlorine atom, a bromine atom), a heterocyclic nucleus (e.g., a morpholynyl group, a piperidyl group), an alkylthio group (e.g., a methylthio group, an ethylthio group), a heterocyclylthio group (e.g., a benzothiazolylthio group), an arylthio group (e.g., a phenylthio group, a tolylthio group), an amino group, an alkylamino group or substituted alkylamino group (e.g., a methylamino group, an ethylamino group, a propylamino group, a dimethylamino group, a diethylamino group, a dodecylamino group, a cyclohexylamino group, a β-hydroxyethylamino group, a di(β-hydroxyethyl)amino group, a β-sulfoethylamino group), an arylamino group or substituted arylamino group (e.g., an anilino group, an o-sulfoanilino group, a m-sulfoanilino group, a sulfoanilino group, an o-anisylamino group, a m-anisylamino group, a p-anisylamino group, an o-toluidino group, a m-toluidino group, a p-toluidino group, an o-carboxyanilino group, a m-carboxyanilino group, a p-carboxyanilino group, a hydroxyanilino group, a disulfophenylamino group, a naphthylamino group, a sulfonaphthylamino group), a heterocycloamino group (e.g., a 2-benzothiazolylamino group, a 2-pyridylamino group), an aryl group ((e.g., a phenyl group), or a mercapto group; $B_1$, $B_2$, $B_3$ and $B_4$ each may be the same or different; when —A— contains no sulfo group, at least one of $B_1$, $B_2$, $B_3$ and $B_4$ should contain at least one sulfo group (which may be a free acid group or form a salt).

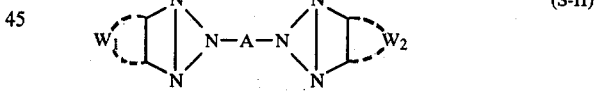

wherein A has the same significance as in formula (S); $W_1$ and $W_2$ each represents the carbon atoms for completing a benzene ring or a naphthalene ring where the benzene ring or naphthalene ring may be substituted and at least one of these substituents, if any, should contain a sulfo group.

Specific examples of compounds represented by the above formulae (S-I) and (S-II) are shown below.

Compound 1

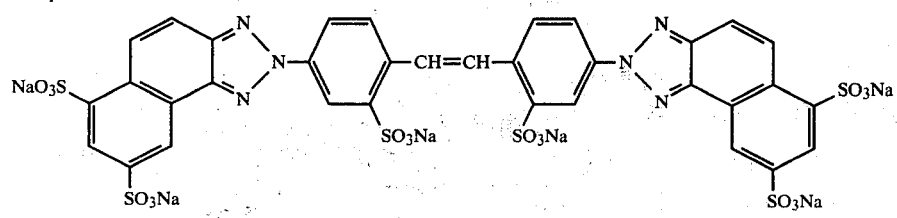

-continued
Compound 2
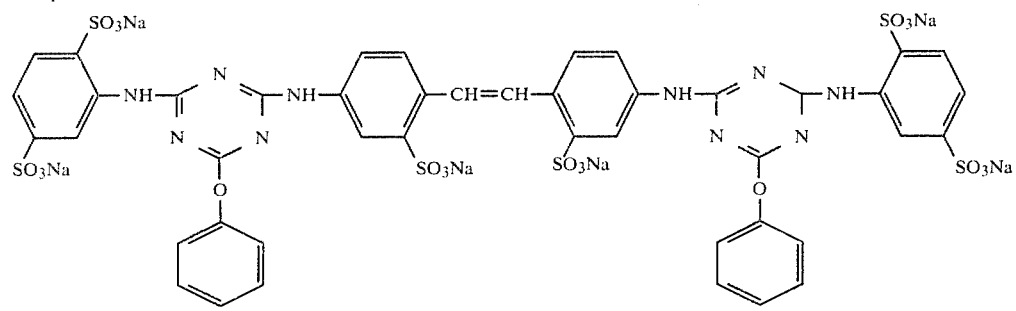
Compound 3
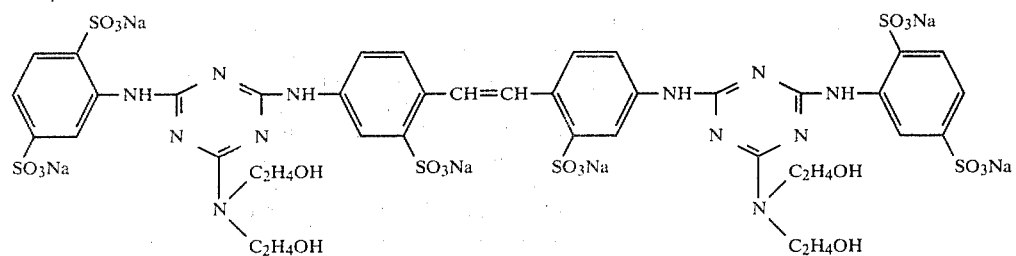
Compound 4
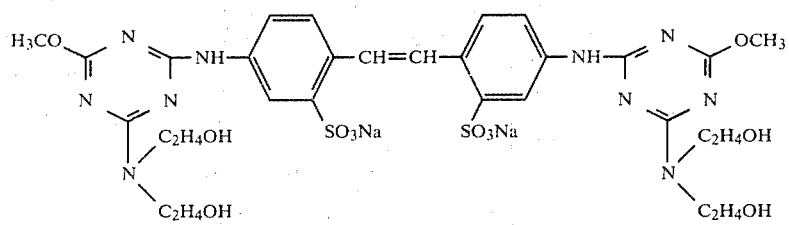
Compound 5
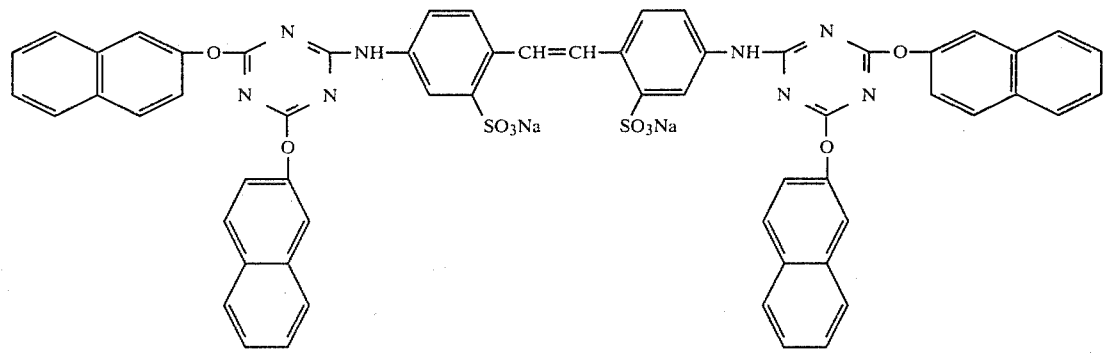
Compound 6
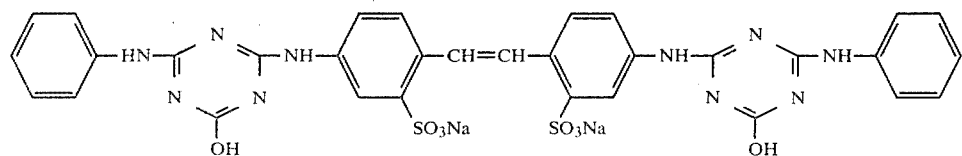
Compound 7
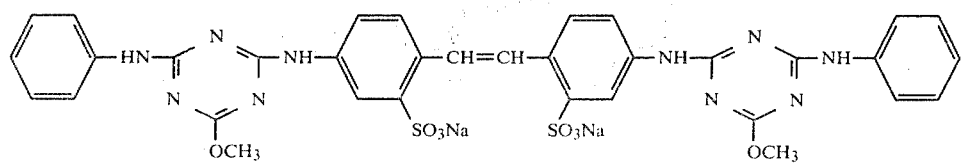

Compound 8
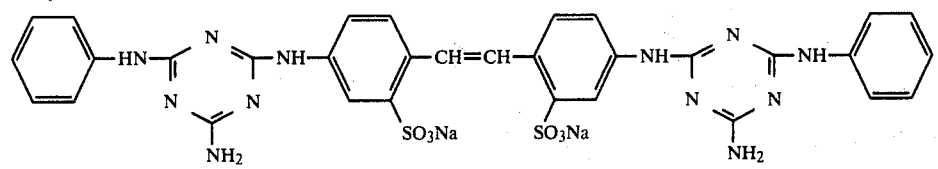
Compound 9
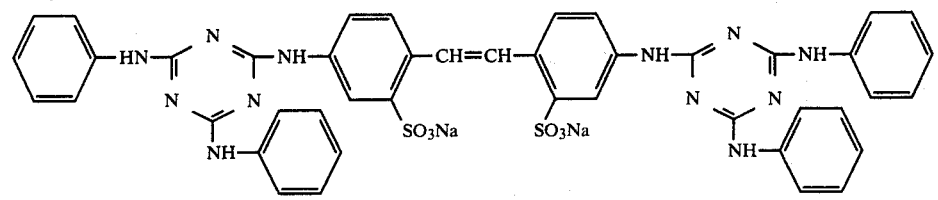
Compound 10
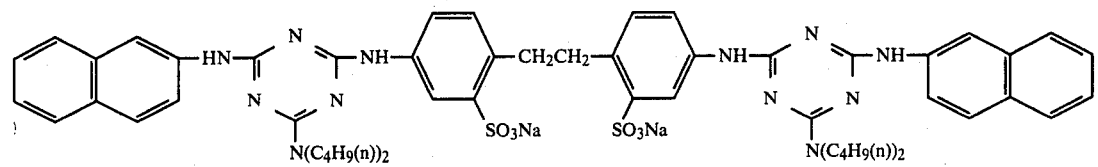
Compound 11
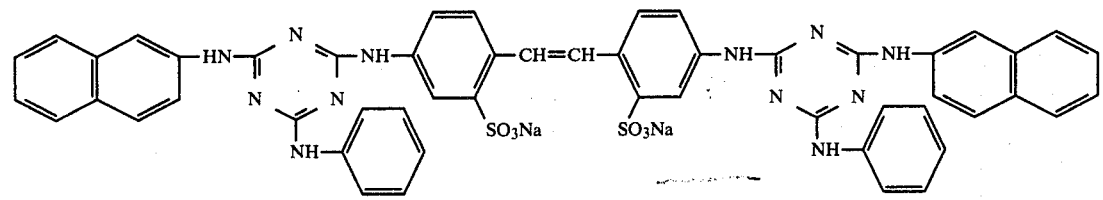
Compound 12
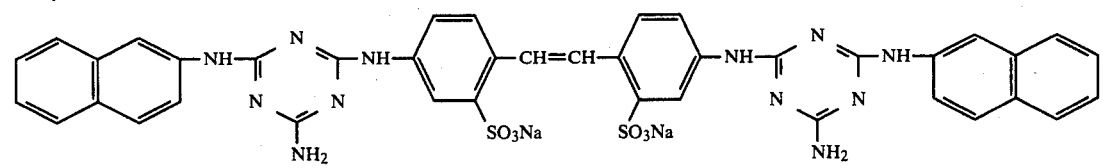
Compound 13
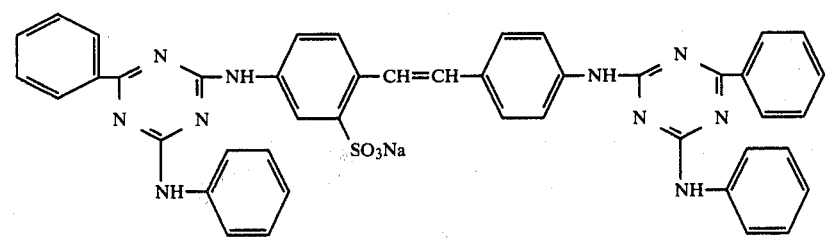
Compound 14
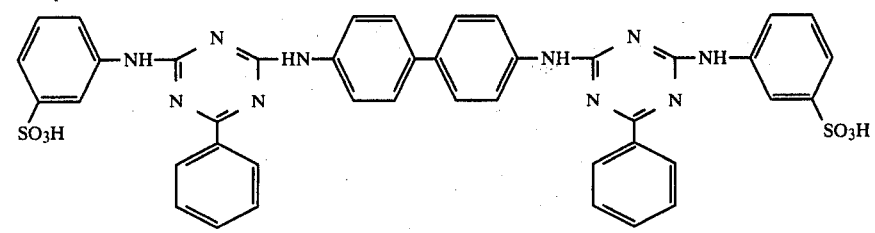

-continued
Compound 15
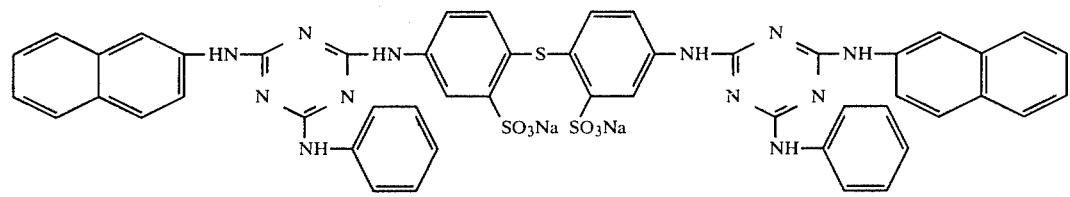
Compound 16
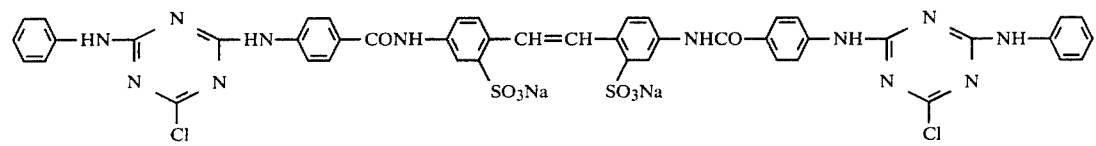
Compound 17
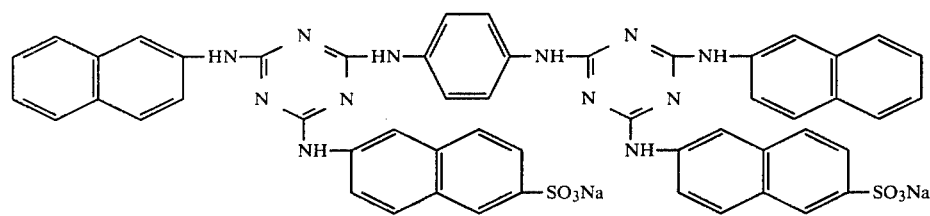
Compound 18
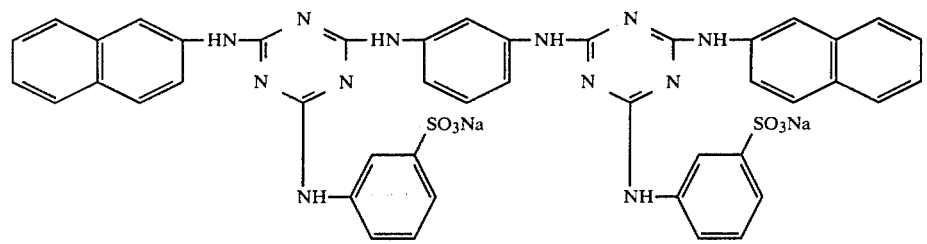
Compound 19
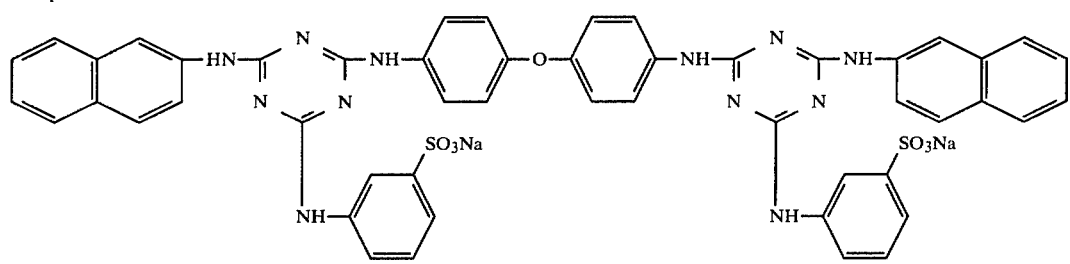
Compound 20
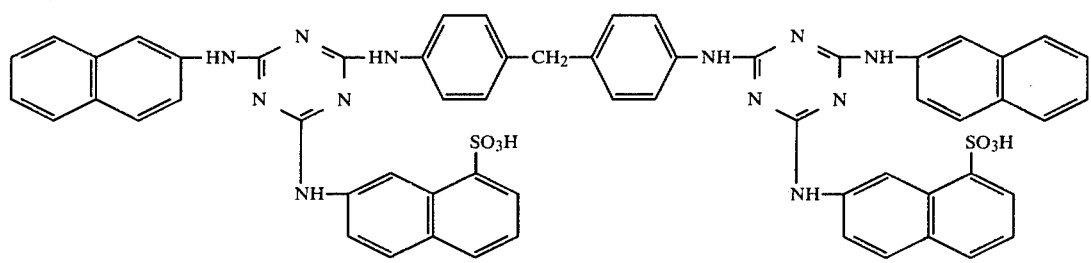

Compound 21
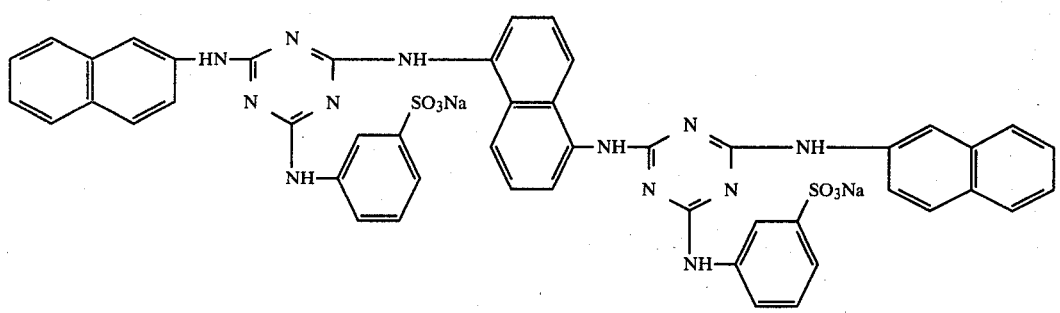
Compound 22
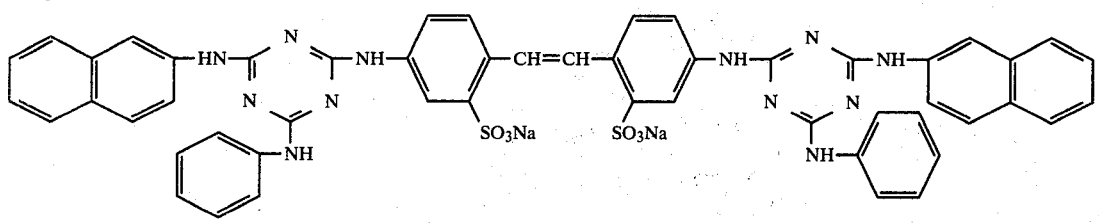
Compound 23
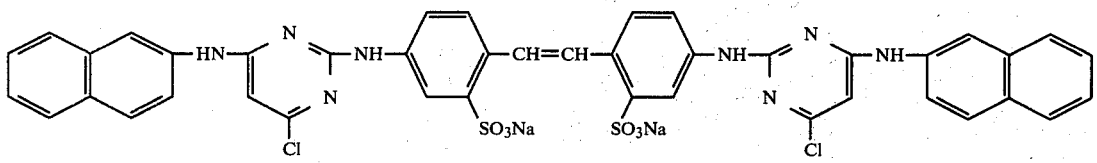
Compound 24
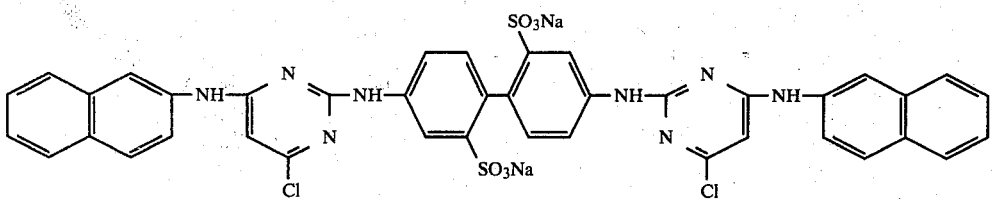
Compound 25
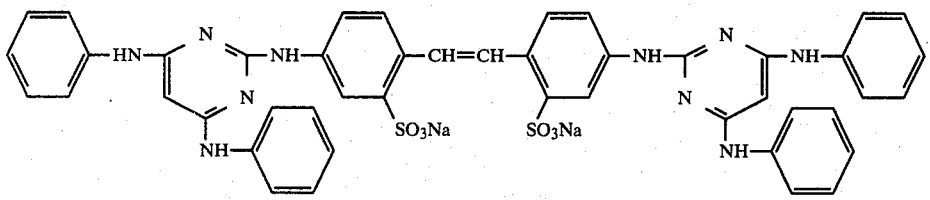
Compound 26
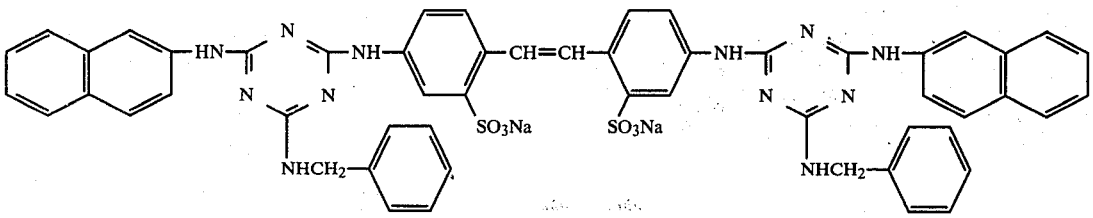

-continued
Compound 27
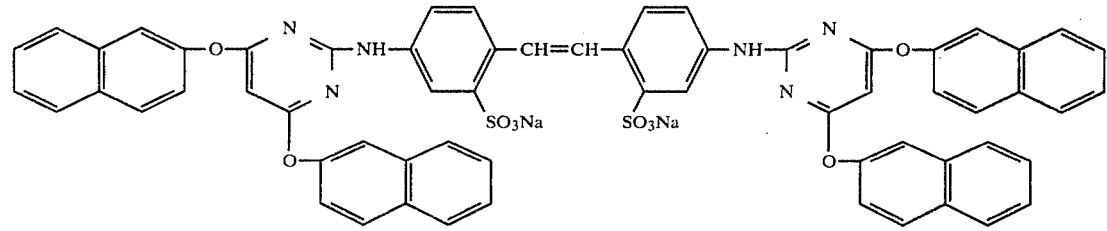
Compound 28
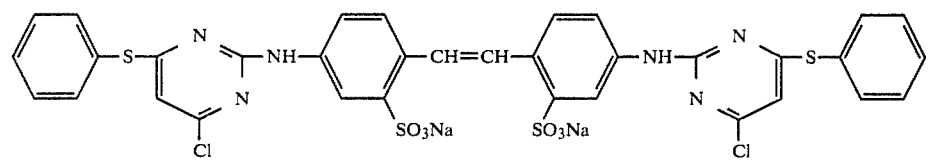
Compound 29
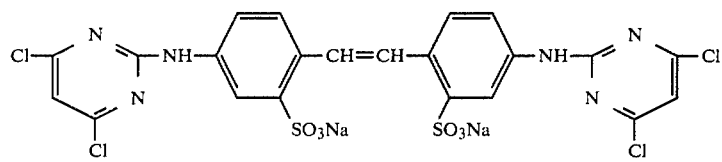
Compound 30
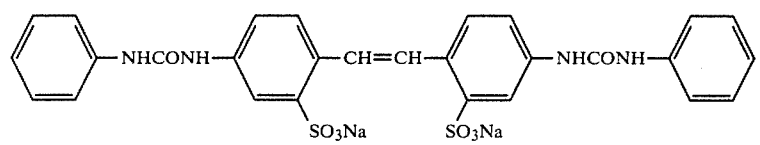
Compound 31
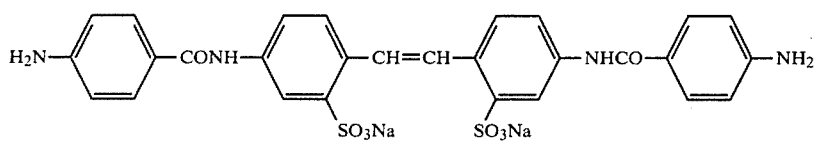
Compound 32
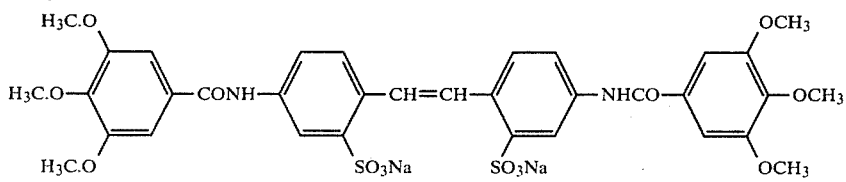
Compound 33
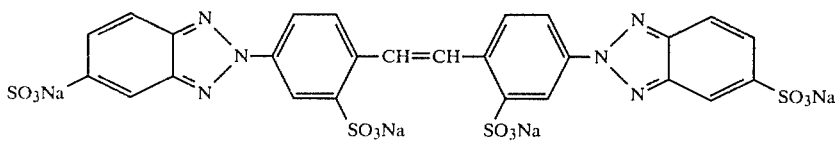
Compound 34
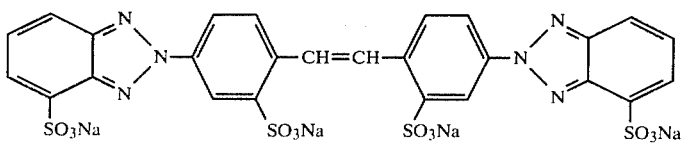

Compound 35

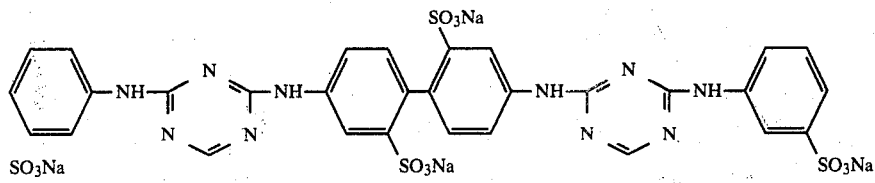

Compound 36

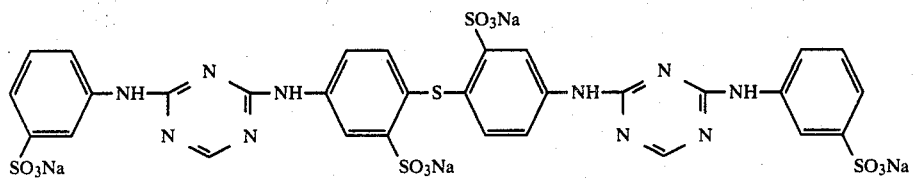

The compound represented by formula (S) is preferably employed in the form of a water containing solution of a 0.0001 to 1 wt% concentration, more preferably as a water containing solution of from 0.001 to 0.01 wt% concentration.

Further, it is preferred that the trace component labelled with the spectral sensitizer be present in an amount of not less than $10^{-12}$ g/ml, more preferably not less than $10^{-11}$ g/ml, in the reagent for measuring the trace component, when the labelled component is employed in an aqueous medium.

Trace components which can be assayed by methods (I) and (II) of this invention are typically trace components in the living body; drugs, in addition thereto, those amenable to analysis.

Examples of such trace components include peptide hormones (e.g., insulin, glucagon, parathyroid hormone, carcitonin, erythoropoietin, secretin, cholecystokinin, gastrin, angiotensin II, vasopressin, oxytocin, melanocytestimulating hormone, adrenocorticotropic hormone, growth hormone, prolactin, luteining hormone, follicle-stimulating hormone); non-peptide hormones (e.g., steroid hormones such as glucocorticoid, aldosterone, adrenergic androgene, estrogene, progesterone, testosterone), or other hormones such as thyroid hormones (e.g., thyroxine, triiodothyronine), cortisol, estriol, adrenaline, noradrenaline, melatonine, acetylcholine, enzymes, e.g., lysozyme, $C_1$ esterase, alkali phosphatase, pepsinogen, trypsin, kinase, virus, specific antigens, tumor antigens, e.g., α-fetoprotein, serum protein components, e.g., thyroxine-bound globulin, 2-microglobulin, IgG, IgE, IgM, IgA, human lysozyme; drugs (e.g., LSD, etc.); and others (e.g., rheumatoid factor, $B_s$ antigen, $B_s$ antibody, myosin, etc.).

In preparing these traces components labelled with a spectral sensitizer, the trace components can be employed as raw materials as they are, but substances (derivatives from natural substances or synthesized substances) having an immune reactivity equivalent to these trace components, which are derived therefrom, can also be employed.

In this invention, an amount of a testing sample spotted onto the analysis element is preferably in the range of from 5 μl to 100 μl, more preferably 10 μl to 50 μl. In the case of contacting a large quantity of testing sample with silver halide a, passing technique can be utilized if necessary.

The analysis element used for the immunochemical measurement of this invention basically comprises a support having provided thereon a silver halide-containing layer; in addition, the analysis element can further comprise a protective layer, a layer of B/F separation (separation layer), a filter layer, etc., depending upon necessity or preference. The protective layer is composed of, e.g., gelatin or a synthetic or semisynthetic polymer and is generally provided on the emulsion layer.

As the filter layer, those disclosed in U.S. Ser. No. 126,920 filed Mar. 3, 1980 now U.S. Pat. No. 4,337,063 can also effectively be used in this invention.

If desired or necessary, an optical filter layer can also be provided in the analysis element of this invention.

Further, a neutralizing layer and a temperature-compensating polymer layer can also be provided in the analysis element used for the measurement of this invention, if necessary or desired. By the provision of such layers, variations in the density of developed silver of colored dye due to changes in processing temperature can be substantially eliminated even if development processing does not proceed at a constant temperature when the analysis element is developed. More specifically, development can be conducted in the presence of a coated layer composed of an acidic polymer layer as disclosed in, e.g., U.S. Pat. Nos. 3,362,819 and 4,028,103, and a temperature-compensating polymer layer as described in U.S. Pat. Nos. 4,056,394 and 4,061,496 and Japanese Patent Application OPI 72622/78, in combination.

Another preferred example of an analysis element of this invention comprises: a support such as a cellulose acetate layer, a polyester layer, a paper sheet laminated with polyethylene, which is surface treated for purpose of preventing peeling between the support and a coated layer provided thereon, in succession or by a simultaneous multicoating technique, the aforesaid water absorbing layer, a silver halide emulsion layer, a protective layer and/or a separation layer.

In the analysis element used for the measurement of this invention, a gelatin and/or polymer layer can be provided at the back surface of the support (opposite the emulsion layer), for purpose of preventing curling under high humidity or low humidity.

The emulsion layer contained in the analysis element is a layer containing silver halide.

Specific examples of silver halides employed in this invention include silver chloride, silver chlorobromide, silver bromide, silver iodobromide, silver chloroiodobromide, silver chloroiodide, silver iodide, etc.

These silver halides can be emulsion dispersed or suspended in hydrophilic colloid binder solution or can be supported on a support without any binder (e.g., a silver halide layer can be directly formed on a support by vacuum deposition, etc.).

The amount of silver halide contained in the silver halide layer used for this invention is preferably in the range of from about 0.5 to about 6.0, more preferably about 1.5 to about 4.5, expressed as optical density after development processing.

Silver halide as disclosed in U.S. Ser. No. 126,920 filed Mar. 3, 1980 now U.S. Pat. No. 4,337,063 can be used as the silver halide in the silver halide layer in this invention.

Silver halide(s) contained in a photographic emulsion used in the present invention can be prepared in a conventional manner, e.g., by a single jet method, a double jet method, or a combination thereof. Useful preparation methods of silver halide emulsions are described in, e.g., Trivelli and Smith, *The Photographic Journal*, vol. 79, pp. 330–338 (1939), C. E. K. Mees, *The Theory of the Photographic Process*, 1966, published by MacMillian, Glafkides, *Photographic Chemistry*, vol. I, pp. 327–336, published by Fountain Press, etc.

The grain size of silver halide(s) in an emulsion(s) employed in this invention is conventional or smaller. It is thus generally preferred that the average grain diameter be 0.04 to 4 microns (e.g., by measurement of number average by the projected area method).

The silver halide emulsions employed in this invention are not chemically ripened but generally are chemically sensitized in a conventional manner, for example, by gold sensitization (as disclosed in U.S. Pat. Nos. 2,540,085, 2,597,876, 2,597,915 and 2,399,083, etc.), by sensitization with metal ions of Group VIII of the Periodic Table, by sulfur sensitization (as disclosed in U.S. Pat. Nos. 1,574,944, 2,278,947, 2,440,206, 2,410,689, 3,189,458 and 3,415,649, etc.), by reduction sensitization (as disclosed in U.S. Pat. Nos. 2,518,698, 2,419,974 and 2,983,610, etc.), or by a combination thereof.

Specific examples of chemical sensitizers include sulfur sensitizers such as allylthio carbamide, thiourea, sodium thiosulfate, cystine, etc.; noble metal sensitizers such as potassium chloroaurate, aurous thiosulfate, potassium chloropalladate, etc.; reduction sensitizers such as stannous chloride, phenylhydrazine, reductone, etc.; polyoxyethylene derivatives as described in British Pat. No. 981,470, Japanese Patent Publication 31-6475 and U.S. Pat. No. 2,716,062, etc.; polyoxypropylene derivatives, quaternary ammonium-containing derivatives, etc.

Silver halide emulsions which are employed in this invention can also contain suitable antifoggants and stabilizers. For example, specific antifoggants and stabilizers include thiazolium salts as described in U.S. Pat. Nos. 2,131,038 and 2,694,716, etc.; azaindenes as described in U.S. Pat. Nos. 2,886,437 and 2,444,605, etc.; urazoles as described in U.S. Pat. No. 3,287,135, etc.; sulfocatechols as described in U.S. Pat. No. 3,236,652, etc.; oximes as described in U.S. Pat. Nos. 2,403,927, 3,266,897 and 3,397,987, etc.; nitron; nitroindazoles; polyvalent metal salts as described in U.S. Pat. No. 2,839,405, etc.; thiuronium salts as described in U.S. Pat. No. 3,220,839, etc.; salts of palladium, platinum and gold as described in U.S. Pat. Nos. 2,566,263 and 2,597,915, etc.

Silver halide emulsions which are used in this invention can also contain, if desired, one or more developing agents (e.g., hydroquinones, catechols, aminophenols, 3-pyrazolidones, ascorbic acid or derivatives thereof, reductones, phenylenediamines, etc.), or combinations of these developing agents. The developing agents can be incorporated into a light sensitive emulsion and/or other suitable layers (e.g., a hydrophilic binder layer) of a photographic element. The developing agents can be incorporated using a suitable solvent or in the form of a dispersion as described in U.S. Pat. No. 2,592,368 or French Pat. No. 1,505,778.

Silver halide emulsions employed in this invention can contain coating aids such as saponin, alkylaryl sulfonates as described in U.S. Pat. No. 3,600,831, etc., amphoteric compounds as described in U.S. Pat. No. 3,133,816, etc., and can further contain antistatic agents, plasticizers, fluorescent whitening agents, developing accelerating agents, air antifogging agents, color toning agents, etc.

As the silver halide emulsion(s) used in this invention, gelatino silver halide emulsions are generally employed but this is not mandatory. For example, instead of gelatin substances that do not adversely affect light sensitive silver halides and are as used for the water absorbing layer can be employed.

Photographic emulsion layers of photographic light sensitive materials used in this invention can contain color image-forming couplers, that is, compounds capable of forming dyes by reaction with the oxidation product of an aromatic amine (normally a primary amine) developing agent (hereafter referred to as a coupler). It is preferred that the coupler be non-diffusible and comprise a hydrophobic group(s) called a ballast group(s) in the molecule thereof. The coupler(s) can be four-equivalent of two-equivalent to silver ions. In addition, the photographic emulsion layers can also contain colored couplers having a color correction effect or couplers releasing a development inhibitor upon development (DIR couplers). The couplers also can be couplers where the product of the coupling reaction is colorless.

To form the silver halide layer of the analysis element used in this invention, conventional techniques in the photographic art can be utilized and details are described in *COATING TECHNOLOGY*, Yuji Harazaki, published by Asakura Publishing Co., Ltd., 1972, etc. For coating the silver halide emulsion(s), a dip coating method, a roller coating method, a curtain coating method, an extrusion coating method, etc., can be employed.

Other layers such as the water absorbing layer, auxiliary layers, etc., can be provided in a similar manner.

Upon coating, coating aids can be employed. Examples thereof are non-ionic surface active agents such as saponin (steroid type), polyalkylene glycol alkylamines or amides, polyethylene oxide adducts of silicone, glycidol derivatives (e.g., alkenylenesuccinic acid polyglycerides, alkylphenol polyglycerides), aliphatic acid esters of polyvalent alcohols, alkyl esters, urethanes or ethers of sugars, etc.; anionic surface active agents containing acidic groups such as carboxy, sulfo, phospho, sulfato, phosphato, etc., such as triterpenoid type saponin, alkyl carbonates, alkyl sulfonates, alkylbenzene sulfonates, alkylnaphthalene sulfonates, alkyl sulfates, alkyl phosphates, N-acyl-N-alkyltaurines, sulfosuccinates, sulfoalkyl polyoxyethylene alkylphenyl ethers, polyoxyethylene alkyl phosphates, etc.; amphoteric surface active agents or phosphates, alkyl betaines, amine imides, amine oxides, etc.; cationic surface active agents such as alkyl amine salts, aliphatic or aromatic quaternary ammonium salts, heterocyclic quaternary ammonium salts such as pyridinium or imidazolium, etc., phosphonium or sulfonium salts containing an aliphatic or heterocyclic ring, etc.

As a support for the analysis element of this invention, flexible supports such as a plastic film, paper, cloth, etc. or rigid supports such as glass, porcelain, metal, etc. can be used. Useful examples of flexible supports include a film composed of semisynthetic or synthetic high molecular weight substances such as cellulose nitrate, cellulose acetate, cellulose acetate butyrate, polystyrene, polyvinyl chloride, polyethylene terephthalate, polycarbonate, etc.; a baryta paper layer, a paper sheet having coated thereon or laminated therewith olefinic polymers (e.g., polyethylene, polypropylene, ethylene-butene copolymers, etc.), or the like.

The surfaces of these supports can be subjected to a subbing treatment for improving adhesion to the silver halide layer. Further, a corona discharge, UV radiation or a flame treatment can also be performed, prior to or after the subbing treatment.

In the method of this invention, exposure is performed as follows.

A variety of light sources can be employed for exposing the silver halide brought into contact with the spectral sensitizer In any case, only light having a wavelength(s) that the spectral sensitizer alone absorbs is employed for exposure, excluding wavelengths in the absorption region intrinsic to silver halide. A suitable exposure degree is generally from $10^1$ to $10^{10}$ cms. As light sources, for example, a tungsten lamp, a halogen lamp, a mercury lamp, a xenon lamp, etc. can be employed in combination with a suitable optical filter (e.g., a sharp cut filter manufactured by Fuji Photo Film Co., Ltd.). In addition, a solid laser (e.g., a ruby laser, etc.), a semiconductor laser (e.g., a lead sulfide laser, etc.), a dye laser, a gas laser (e.g., a neon helium laser, an argon laser, etc.) and the like can be advantageously employed.

In this invention, it is preferred that when a transparent film (support) having the emulsion layer thereon is used, exposure be performed through the support to the emulsion layer. Upon exposure, it is necessary to employ a light source having overlaid thereon an optical filter to absorb light having wavelengths in the absorption region intrinsic to silver halide, or to use light from which wavelengths in the absorption region intrinsic to silver halide have been filtered out. It is particularly preferred that exposure be performed through a light source having overlaid thereon an optical filter which mainly transmits light of wavelengths that the spectral sensitizer absorbs.

The emulsion layer exposed as described above is then processed by conventional photographic processing. That is, in the case where the emulsion(s) is coated on a support, development processing techniques as are conventionally used for processing ordinary photographic films or printing paper can be utilized. Further, photographic processing can also be effected by developing, coating or spraying processing solutions on a support having coated thereon the emulsion(s), or dipping the support in processing solutions. Photographic processing can also be performed by incorporating or mixing processing solutions into or with a liquid type emulsion.

When the hydrazine compound shown by formula (H) is present for further enhancing detection sensitivity, development processing is performed in the presence of the hydrazine compound. More specifically, (1) the hydrazine compound is incorporated in at least one hydrophilic colloid layers in the silver halide light sensitive layer-containing analysis element of this invention, or (2) the hydrazine compound is incorporated in a photographic pre-bath prior to development processing, a developer or a buffer solution employed for the immune reaction.

The development processing temperature is generally selected between 18° and 50° C., but can be lower than 18° C. or higher than 50° C. Depending upon the purpose, any development processing forming silver images (black-and-white photographic processing) and color photographic processing comprising development processing to form color images can be used.

The optical density or degree of blackening increases with increase in processing temperature. Accordingly, it is desired that processing be performed at a constant temperature. However, instead of using constant temperature processing, a technique in which the optical density or degree of blackening is not substantially changed by using the aforesaid neutralizing layer and temperature-compensating layer in combination is also effective.

Developing solutions used in the case of black-and-white photographic processing can contain known developing agents. As such developing agents, dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, and heterocyclic compounds comprising a condensed 1,2,3,4-tetrahydroquinoline ring and an indolene ring as described in U.S. Pat. No. 4,067,872, etc., can be used singly or as a combination thereof.

The developing agent solutions can generally contain known preservatives, alkali agents, pH buffers, antifogging agents, and, if necessary, dissolution aids, color toning agents, development accelerators, surface active agents, defoaming agents, softening agents, hardening agents, viscosity-imparting agents, etc.

"Lith" type development processing can also be applied to the photographic emulsion of this invention. The term "lith" type development processing refers to development processing which comprises, for the purpose of photographic reproduction of line images or photographic reproduction of half tone images using dots, infectious development at a low concentration of sulfite ions generally using a dihydroxybenzene(s) as a developing agent, the details of which are given in *Photographic Processing Chemistry*, Mason, 163-165 (1966).

As a special aspect of development, a developing method which comprises treating a light sensitive material in which a developing agent is contained, e.g., in an emulsion layer, in an aqueous alkaline solution can be used. Of such developing agents, a hydrophobic type can be incorporated into an emulsion layer by latex dispersion, as disclosed in *Research Disclosure*, No. 169, RD-16928. Such development processing can also be used in combination with silver salt stabilization, e.g., with a thiocyanate(s).

As fixing solutions, those having compositions conventionally used in photographic processing can be employed, e.g., as fixing agents, organic sulfur compounds such as thiosulfates, thiocyanates and other organic sulfur compounds that are known as having a fixing effect can be employed. The fixing solution can also contain water soluble aluminum salts as a hardening agent.

To form dye images, again conventional methods are used. A nega-posi method (e.g., as described in *Journal of the Society of Motion Picture and Television Engineers*, vol. 61, 667–701 (1953) can also be used; further, a color reversal method which comprises developing with a developer containing a black-and-white developing agent to form negative silver images, then performing at least one overall exposure or other suitable fogging treatment and subsequently color developing to obtain positive color images can also be used; also, a silver dye bleach method which comprises exposing a photographic emulsion layer containing a dye, developing to thereby form silver images, and then bleaching the dye using the silver images as a bleaching catalyst, etc., can be used.

In general, a color developer comprises an aqueous alkaline solution containing a color developing agent. As color developing agents, known primary aromatic amine developing agents, for example, phenylenediamines (e.g., 4-amino-N,N-diethylaniline, 3-methyl-4-amino-N,N-diethylaniline, 4-amino-N-ethyl-N-beta-hydroxyethylaniline, 3-methyl-4-amino-N-ethyl-N-beta-hydroxyethylaniline, 3-methyl-4-amino-N-ethyl-N-beta-methanesulfamidoethylaniline, 4-amino-3-methyl-N-ethyl-N-beta-methoxyethylaniline, etc.) can be used.

In addition, compounds as described in L. F. A. Mason, *Photographic Processing Chemistry*, 226–229, 1966, Focal Press; U.S. Pat. Nos. 2,193,015 and 2,592,364; and Japanese Patent Application Laid Open OPI No. 48-64933, etc., can be used.

The color developer can also contain a pH buffering agent such as a sulfite, carbonate, borate and phosphate of an alkali metal, a development inhibitor or an antifogging agent such as a bromide, iodide or an organic antifogging agent, etc. The color developer can also contain, if desired or necessary, a hard water softener, a preservative such as hydroxylamine, an organic solvent such as benzyl alcohol or diethylene glycol; a development accelerator such as polyethylene glycol, a quaternary ammonium salt or an amine; a dye forming coupler, a competing coupler, a fogging agent such as sodium borohydride, an auxiliary developing agent such as 1-phenyl-3-pyrazolidone, a viscosity imparting agent, a polycarboxylic acid type chelating agent as described in U.S. Pat. No. 4,083,723, an antioxidant as described in German Patent Application (OLS) 2,622,950, etc. Of course, combinations of the above materials can also be used.

The photographic emulsion layer(s) after color development is/are usually subjected to bleaching. Bleaching can be performed with fixing at the same time or separately therefrom. Representative examples of bleaching agents include polyvalent metal compounds of iron (III), cobalt (III), chromium (VI), copper (II), etc., peroxides, quinones, nitroso compounds, etc. For example, ferricyanides, bichromates, inorganic complexes of iron (III) or cobalt (III), aminopolycarboxylic acids such as ethylenediamine tetraacetic, acid, nitrilotriacetic acid, 1,3-diamino-2-propanol tetraacetic acid, etc., complexes of organic acids such as citric acid, tartaric acid, maleic acid, etc.; persulfates, permaganates; nitrosophenol, etc., can be employed. Of these, potassium ferricyanide, ethylene diamine tetraacetic acid iron (III) sodium and ethylene diamine tetraacetic acid iron (III) ammonium are particularly useful both in an independent bleaching solution and in a mono bath bleaching-fixing solution.

The bleaching or blix solutions can also contain bleach accelerators as described in U.S. Pat. Nos. 3,042,520 and 3,241,966 and in Japanese Patent Publications Nos. 45-8506 and 45-8836, etc., thiol compounds as described in Japanese Patent Application Laid Open (OPI) No. 53-65732 and other various additives.

Processing solutions used in this invention can be liquid compositions containing processing components necessary for the development of silver halide emulsions and the formation of diffusion transfer dye images in which the major portion of the solvent is water and wherein a hydrophilic solvent(s) such as methanol, methyl cellosolve, etc., can also optionally be present in addition to water.

The processing composition should have a pH necessary for development of the emulsion layers and should contain alkali in an amount sufficient to neutralize acids (e.g., hydrogen halides such as hydrogen bromide, carboxylic acids such as acetic acid, etc.) released during various steps for developing and forming dye images. As the alkali, alkali metal or alkaline earth metal salts, e.g., lithium hydroxide, sodium hydroxide, potassium hydroxide, a calcium hydroxide dispersion, hydroxylated tetramethyl ammonium, sodium carbonate, trisodium phosphate, diethyl amine, etc., or other amines are illustrative. Preferably, the alkali is an alkali hydroxide and imparts a pH of at least about 12 at room temperature, more preferably a pH of at least 14.

More preferably, the processing compositions contain hydrophilic polymers such as high molecular weight polyvinyl alcohol, hydroxyethyl cellulose, sodium carboxymethyl cellulose and the like. These polymers impart a viscosity of at least 1 poise at room temperature, preferably several hundred (500 to 600) to 1000 poise to the processing compositions to thereby not only provide uniform development upon processing but also to permit easy transfer of aqueous solvent into the light sensitive element and an image receiving element during processing, where, when the processing compositions are concentrated, a non-fluid layer can be formed to assist formation of a film unit which is finely united after processing. Such a hydrophilic polymer layer prevents, after the formation of a diffusion transfer color image is substantially complete, further transfer of colored component into the image receiving layer to thereby help prevent image changes.

In some cases, it is advantageous that the processing compositions also contain light absorbing substances such as $TiO_2$ or carbon black, pH indicators, or desensitizers as described in U.S. Pat. No. 3,579,333, in order to prevent a silver halide(s) from being fogged by an external light. In addition, the processing compositions can also contain development inhibitors such as benzotriazole. The aforesaid processing compositions can be used by encasing the same in a rupturable container as described in U.S. Pat. Nos. 2,543,181, 2,653,732, 2,723,051, 3,056,491, 3,056,492 and 3,152,515, 2,643,886, etc.

According to the method of this invention, detection sensitivity of trace components is high and excellent results with precise accuracy and reproducibility are obtained.

The markers used in the method of this invention do not involve the hazards of radiation as does radioimmunoassay since the markers, i.e., spectral sensitizers, are not radioactive; measurement and inspection can easily be performed by a person not necessarily qualified to deal with radioactives and, in addition, storage of the labelling substances for a long period of time is possible due to their excellent stability. Further, densitometers as are conventionally used in the photographic arts can be used as measurement equipment so that measurement can be made simply and at low cost.

Having thus generally described this invention, the following working examples illustrate currently preferred modes of practicing this invention. In the following examples, percentages are all by weight, unless otherwise indicated.

EXAMPLE 1

Synthesis of insulin labelled with spectral sensitizer

In 1 ml. of 4 mol/l urea, 20 mg. of purified pork insulin (purchased from Sigma Chemicals Co., Ltd.) was dissolved. To the solution, 8 ml. of DMF (dimethyl formamide) was further added. The mixture was stirred under ice-cooling (0° to 4° C.) (Liquid A).

Spectral sensitizer (I)

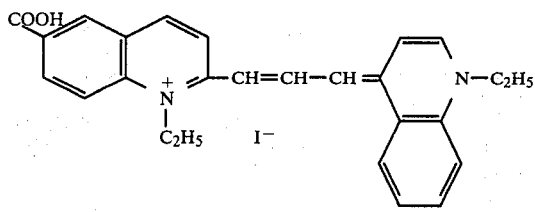

Spectral sensitizer (I) of formula above (5 mg.) was dissolved in 2 ml. of DMF. Three sets of the solution were prepared under cooling at −15° to −20° C., 5 μl each of isobutyl chloroformate and 1.5 μl each of triethyl amine were added to the solutions, and 2 mg. each of hydroxysuccinimide was further added under still cooling (Liquid B).

Thereafter, Liquid B was added to Liquid A with stirring under ice-cooling (4° C.) and the mixture was reacted. After reacting for 30 mins. under ice-cooling and 30 mins. at room temperature, the reaction mixture was desalted with Sephadex G-10 column equilibrated with 0.2 N ammonia water. Fractions containing sensitizer labelled insulin were collected and then lyophilized. Thus, insulin labelled with the spectral sensitizer was obtained; yield 24.6 mg., $\lambda_{max}^{2\%}$ SDS=660 nm, $\epsilon_{660\ nm} = 3.2 \times 10^5$ In the amino terminal analysis (Dansyl method) of the labelled insulin, glycine and phenylalanine which were the amino terminals of pork insulin were not detected at all. Further in chromatography using a Sephadex G-50 column (equilibrated with 1% SDS), the labelled insulin thus obtained showed a single peak.

Preparation of silver chlorobromide emulsion

To 300 ml. of a 1% gelatin aqueous solution containing 49 g. of KBr and 17 g. of NaCl, 400 ml. of an aqueous solution of 100 g. of AgNO₃ was added at 70° C. After removing by-products (KNO₃, etc.), 5 g. of gelatin and 10 mg. of a chemical sensitizer (Na₂S₂O₃) were added to the mixture in a conventional manner and the mixture was then ripened in a conventional manner. Thus, about 1 kg. of silver chlorobromide emulsion (average grain size, 0.8μ) was obtained.

Standard curve in insulin assay in the presence or absence of hydrazine compound According to a double antibody method in which the pork insulin labelled with the spectral sensitizer described above was used and anti-pork insulin guinea pig serum and anti-guinea pig IgG rabbit serum were used as a primary antibody and a secondary antibody, respectively, a calibration curve corresponding to standard insulin solutions having various concentrations (5 μU/ml to 320 μU/ml) was prepared (in the presence or absence of hydrazine compound) as described below.

0.1 ml. of standard insulin solutions having various concentrations were separately charged in small test tubes and 0.4 ml. of a 0.1 M of tris-hydrochloric acid buffer solution having a pH of 8.5 (Liquid C) containing 0.1 M (mol/l, hereafter the same) NaCl and 1.0% bovine serum albumin (BSA) was further added to the respective test tubes. Further, 0.1 ml. of a diluted solution of anti-pork insulin guinea pig serum, the titer of which had previously been determined, was added to the test tubes, respectively. Then, 0.1 ml. of the insulin labelled with the spectral sensitizer dissolved in and appropriately diluted with Liquid C was added. After thoroughly stirring, the mixture was allowed to stand for 16 hrs. at 4° C. Then, 0.1 ml. of a diluted anti-guinea pig IgG rabbit serum solution was added and the mixture was thoroughly stirred to react for a further 24 hrs. at 4° C. The formed precipitates were removed by centrifugal separation (3000 rpm, 10 mins.).

The resulting supernatants after the centrifugal separation were spotted by 10 μl each at an area of 5 mmφ, respectively, on analysis film (I) obtained by coating unexposed AgBrCl emulsion above described (Cl content 20 mol%, average grain size 0.8μ, thickness about 5 μm) on a TAC (cellulose triacetate; hereafter the same) support. After standing for 15 mins., exposure was performed through an SC-60 filter made by Fuji Photo Film Co., Ltd. at 5000 Lux for 1 sec. The exposed analysis film was developed with Developer A having the formulation indicated below at 20° C. for 10 mins. followed by fixing, washing with water and drying in a conventional manner.

Developer A:
 Metol—0.31 g.
 Hydrogen Sodium sulfite—39.6 h.
 Hydroquinone—6.0 g.
 Sodium carbonate (monohydrate)—21.9 g.
 Potassium bromide—0.86 g.
 Citric acid—0.68 g.
 Potassium metabisulfite—1.50 g.
 Water to make 1 liter The resulting black densities on the analysis film thus obtained were measured with a photographic densitometer made by Fuji Photo Film Co., Ltd. and a calibration curve was prepared based on the data above.

To the same emulsion above, $2.5 \times 10^{-2}$ mol/mol Ag of p-tolylformylhydrazine (Compound H-2) was added. Using analysis film (II) in which the amount of silver coated, layer thickness and Ag/gelatin ratio were identical with those of analysis film (I) using the above emulsion, a calibration curve was prepared using the same supernatants obtained above under the same conditions. Both films are compared in Table 1.

TABLE 1

| Concentration of Insulin ($\mu$U/ml) | Optical Density | |
|---|---|---|
| | Analysis Film(I) | Analysis Film(II) |
| 0 | 0.18 | 0.20 |
| 5 | 0.20 | 0.51 |
| 10 | 0.24 | 0.90 |
| 20 | 0.31 | 1.45 |
| 40 | 0.65 | 1.96 |
| 80 | 1.10 | 2.50 |
| 160 | 1.51 | 3.04 |
| 320 | 1.86 | 3.22 |

From the results above, increased detection density by the addition of the hydrazine compound was clearly observed.

EXAMPLE 2

In 2 ml. of 2 M urea, 50 mg. of human lysozyme (purified from urine of patients with leukemia) was dissolved. To the solution, 6 ml. of DMF was further added and the mixture was stirred under ice-cooling (0° to 4° C.). 2 mg. each of a spectral sensitizer shown by the following structure (II):

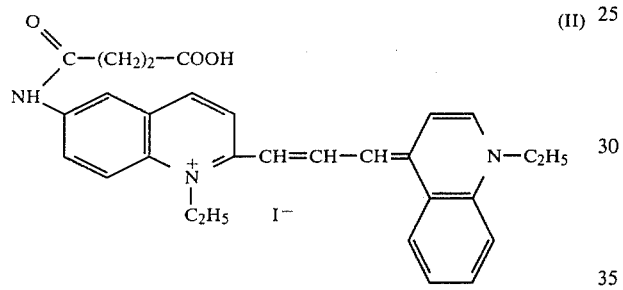

(II)

was weighed in 3 small test tubes and dissolved by adding 2 ml. of DMF thereto, respectively. To the solutions, 2 $\mu$l of isobutyl chloroformate and 1 $\mu$l of triethyl amine were added, respectively, under cooling at $-15°$ to $-20°$ C. to thereby activate -COOH on the spectral sensitizer. Then, the thus activated spectral sensitizer was added to the human lysozyme solutions described above at a 5-minute interval, under ice-cooling and stirring the solutions to thereby cause reaction. After reacting for 30 mins. under ice-cooling, the reaction mixture was desalted with a Sephadex G-10 column equilibrated with 0.2 N ammonia water and then freeze-dried to obtain the human lysozyme labelled with the spectral sensitizer; yield ca. 52 mg., $\lambda_{max}^{2\%SDS}=665$ nm $\epsilon_{665}$ nm$=1.64\times10^5$ In the amino terminal analysis of the thus obtained product lysine which was the amino terminal of human lysozyme was not detected. Further, by chromatography using a Sephadex G-50 column (equilibrated with 1% SDS), the product gave a single peak. Further, in lytic activity using Micrococcus Lysodeikticus cells as a substrate, the product showed almost the same activity as in the unmodified enzyme.

The human lysozyme labelled with the spectral sensitizer was dissolved in a 0.05 M tris-hydrochloric acid buffer solution having a pH of 8.0 and containing 0.1 M NaCl and 1% BSA to prepare solutions having two kinds of concentration of 1 ng/ml and 0.5 ng/ml. Using the solutions, three kinds of analysis films, i.e., I, II and III, were prepared using the same emulsion under the same coating conditions as in Example 1. Three spot solutions having different components were then tested as in Example 1 to examine detection sensitivities of these analysis films and solution components.

Results are shown in Table 2 below.

TABLE 2

| Analysis Film | Hydrazine Compound | | Black Density | | |
|---|---|---|---|---|---|
| | Analysis Film | Spot Solution | Human Lysozyme 1 ng/ml | Human Lysozyme 0.5 ng/ml | Blank |
| I | none | none | 0.35 | 0.21 | 0.18 |
| I | none | H-2 | 0.89 | 0.54 | 0.18 |
| I | none | H-9 | 0.90 | 0.48 | 0.24 |
| II | H-2 | none | 1.06 | 0.59 | 0.17 |
| III | H-9 | none | 1.23 | 0.66 | 0.23 |
| III | H-9 | H-2 | 1.22 | 0.63 | 0.22 |

In Table 2:

H-2: $2.5\times10^{-2}$ mol/mol Ag or 100 mg/l. spot solution

H-9: $2.5\times10^{-4}$ mol/mol Ag or 1 mg/l. spot solution

It is understood from the results above that the presence of the hydrazine compound contributed to a marked increase in black density.

EXAMPLE 3

Analysis films 1 through 6 were prepared using the same emulsion under the same conditions as described in Example 1 except that hydrazine compounds (i.e., H-2, H-9, H-16, H-21 and H-29) were contained in the concentration indicated in Table 3 below in analysis films 2 to 6, respectively; analysis film 1 contained no hydrazine compound.

The thus prepared analysis films were exposed and then processed in the same manner as in Example 1.

The resulting black densities at the spotted areas were measured.

Results are shown in Table 3; wherein the difference ($\Delta$D) in black density refers to a difference in density between the area spotted with the buffer solution alone and the areas spotted with the spot solutions.

The spotted solution was a solution of hyman lysozyme labelled with spectral sensitizer at a concentration of 1 ng/ml.

TABLE 3

| Analysis Film | Hydrazine Compound | Addition Amount | Difference in Black Density($\Delta$D) |
|---|---|---|---|
| 1 | — | — | 0.29 |
| 2 | H-2 | $2\times10^{-2}$ | 0.93 |
| 3 | H-9 | $2\times10^{-4}$ | 1.05 |
| 4 | H-16 | $5\times10^{-3}$ | 0.88 |
| 5 | H-21 | $1\times10^{-2}$ | 0.98 |
| 6 | H-29 | $2\times10^{-1}$ | 1.01 |

As is seen from the results above, these hydrazine compounds were sufficiently effective for increasing the black density.

EXAMPLE 4

Effect of Stabilizer (Compound 1):

A standard curve for insulin was prepared as described in Example 1 except that Compound 1 was added to the system as a stabilizer.

Optical densities obtained are shown in Table 4 below, wherein:

Column A indicates results obtained with analysis film (I) in Example 1;

Column B indicates results obtained with analysis film (II) in Example 1; and,

Column C indicates results obtained with analysis film (III) in which the concentration of the labelled insulin was reduced by a half.

In these cases, the stabilizer (Compound 1) was dissolved in Liquid C at a concentration of 0.05 wt%.

TABLE 4

| Concentration of insulin ($\mu$U/ml) | Optical Density | | |
|---|---|---|---|
| | A Film (I) | B Film (II) | C Film (III) |
| 0 | 0.18 | 0.35 | 0.21 |
| 5 | 0.35 | 0.83 | 0.43 |
| 10 | 0.50 | 1.60 | 0.82 |
| 20 | 0.63 | 2.45 | 1.35 |
| 40 | 0.90 | 2.99 | 1.85 |
| 80 | 1.55 | 3.12 | 2.33 |
| 160 | 2.13 | 3.28 | 2.89 |
| 320 | 2.85 | 3.25 | 3.18 |

The results in Table 4 show that the stabilizer further enhanced the effect of the hydrazine compound. This means that a concentration of the tracer, i.e., the labelled insulin with spectral sensitizer, can be reduced and it is very advantageous since the labelled insulin can be prepared in a complicated manner and its preparation cost is high.

EXAMPLE 5

Effect of other stabilizers:

The spectral sensitizer-labelled insulin produced in accordance with the process described in Example 1 was dissolved (in a concentration of 4 ng/cc ($=10^{-9}$/ml)) in a trishydroxymethylaminomethane-hydrochloric acid buffer solution having dissolved therein 0.005 wt% of Compounds 1 through 5, 35 and 36, respectively, which buffer solutions were adjusted in pH to 8.5. However, Compound 5 was sparingly soluble in water and thus it was dissolved in a 1% 1 N NaOH-99% methanol solvent mixture in a concentration of 0.5%; the resulting solution was diluted with the buffer solution to prepare a 0.05% solution thereof.

25 $\mu$l each of the thus prepared dye-labelled insulin solutions at 4 ng/cc concentration and the buffer solution (blank) free of the insulin were spotted on the analysis film containing the aforesaid silver chlorobromide.

TABLE 5

| Compound | Difference in Optical Density | | Ratio of After 24 hrs. to Immediately after preparation |
|---|---|---|---|
| | Immediately after Preparation | After 24 hrs. | |
| none | 0.70 | 0.12 | 17% |
| 1 | 1.14 | 1.11 | 97% |
| 2 | 1.03 | 0.99 | 96% |
| 3 | 1.10 | 1.08 | 98% |
| 4 | 1.04 | 1.00 | 96% |
| 5 | 0.95 | 0.84 | 88% |
| 35 | 0.98 | 0.92 | 94% |
| 26 | 1.02 | 0.95 | 93% |

By the addition of Compounds 1 to 5, 35 and 36, the decrease in density due to storage of the trace component labelled with the spectral sensitizers was markedly improved. Further, an increase in density, i.e., an increase in detection sensitivity, was also observed.

EXAMPLE 6

The same procedure as in Example 5 was repeated except that 0.1% albumin and 0.1% gelatin were employed, respectively, instead of distilled water.

The density 24 hrs. compared to that immediately after preparation is shown in Table 6.

TABLE 6

| Additive | Difference in Optical Density Ratio of After 24 hrs. to Immediately after Preparation | |
|---|---|---|
| | Albumin | Gelatin |
| none | 60% | 45% |
| Compound 1 | 99% | 98% |
| Compound 2 | 97% | 96% |
| Compound 3 | 100% | 99% |
| Compound 4 | 98% | 96% |
| Compound 5 | 93% | 90% |
| Compound 35 | 97% | 95% |
| Compound 36 | 96% | 95% |

From the results above, the stabilizing effect during storage due to the addition of Compounds 1 to 5, 35 and 36 is clearly seen. Further, albumin or gelatin itself showed a stabilizing effect during storage of the labelled substances.

From comparison with the data in Example 1, it can be seen that storage stability was not decreased even when gelatin or albumin was present with Compounds of formula (S).

EXAMPLE 7

The same procedure as in Example 1 was conducted except that the concentrations of Compounds 1 and 2 were changed to those as indicated in Table 7.

The results are shown in Table 7.

TABLE 7

| Additive | Concentration | Optical Density | | Change in Optical Density After 24 hrs. / Immediately after preparation |
|---|---|---|---|---|
| | | Immediately after preparation | After 24 hrs. | |
| none | — | 0.68 | 0.11 | 16% |
| Compound 1 | wt % | | | |
| | 0.0001 | 0.95 | 0.75 | 79% |
| | 0.001 | 1.08 | 1.04 | 96% |
| | 0.005 | 1.13 | 1.11 | 98% |
| | 0.01 | 1.04 | 1.01 | 97% |
| | 0.1 | 0.74 | 0.70 | 95% |
| | 1 | 0.62 | 0.57 | 92% |
| Compound 2 | wt % | | | |
| | 0.0001 | 0.85 | 0.67 | 79% |
| | 0.001 | 0.97 | 0.93 | 96% |
| | 0.005 | 1.04 | 1.01 | 97% |
| | 0.01 | 0.98 | 0.95 | 97% |
| | 0.1 | 0.70 | 0.65 | 93% |
| | 1 | 0.58 | 0.52 | 90% |

From the results above, it is seen that the decrease in optical density was very slight in the concentration range of from 0.0001 to 1% as compared to the case where no additive was present; that is, the stability of the labelled substances was improved. In particular, the stabilizing effect was remarkable in the range of from 0.001% to 0.1%.

While the invention has been described in detail and with reference to specific embodiments thereof, it will be apparent to one skilled in the art that various changes and modifications can be made therein without departing from the spirit and scope thereof.

What is claimed is:

1. In a photochemical measurement method of a trace component(s) utilizing an immunological reaction which comprises:

labelling an antigen or antibody with a spectral sensitizer, competitively reacting said antigen or antibody labelled with a spectral sensitizer and an antigen or antibody to be measured with an antibody or antigen which specifically reacts with the respective antigen or antibody, bringing either the reaction product or the unreacted component into contact with silver halide, exposing the resulting product to light having a wavelength which said spectral sensitizer absorbs, photographically developing the exposed silver, and, measuring the resulting optical density of the formed silver image and/or colored dye formed by the photographic development, said contact with silver halide being performed in the presence of a hydrazine compound of formula (H):

(H)

wherein $R^{1h}$ is an aryl group and $R^{2h}$ is a hydrogen atom, an alkyl group or an aryl group.

2. The photochemical measurement method of claim 1 wherein said hydrazine compound is incorporated into a silver halide light sensitive material in the range of from $10^{-8}$ to $10^{-1}$ mol/mol Ag.

3. The photochemical measurement method of claim 1 wherein said hydrazine compound is incorporated in a photographic pre-bath, a photographic developer or a buffer solution in the range of from 5 mg. to 15 g. per 1 liter thereof.

4. The photochemical measurement method of claim 1 wherein said spectral sensitizer has an absorption region at a longer wavelength than the absorption wavelength region intrinsic to silver halide.

5. The photochemical measurement method of claim 1, 2, 3 or 4 wherein said antigen or antibody labelled with a spectral sensitizer is dissolved in an aqueous medium in the presence of a compound of formula (S):

$$D_1—A—D_2 \quad (S)$$

wherein $D_1$ and $D_2$ each represents a condensed polycyclic aromatic heterocyclic residue or an aromatic heterocyclic nucleus-substituted amino group and —A— represents a divalent aromatic residue; at least one of $D_1$, $D_2$ or —A— containing an —$SO_3M$ group wherein M represents a hydrogen atom, an alkali metal or an ammonium group.

6. The photochemical measurement method of claim 5 wherein said compound of formula (S) is represented by formula (S-I):

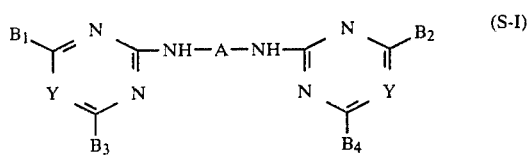

wherein A is a divalent aromatic residue; Y is =CH—, =CB$_5$— or =N— wherein B$_5$ represents a lower alkyl group or a halogen atom; B$_1$, B$_2$, B$_3$ and B$_4$ each represents a hydrogen atom, a hydroxy group, an alkoxy group, a lower alkyl group, an aryloxy group, a halogen atom, a heterocyclic nucleus, an alkylthio group, a heterocyclylthio group, an arylthio group, an amino group, an alkylamino group, an arylamino group, a heterocyclylamino group, an aryl group or a mercapto group; at least one of A, B$_1$, B$_2$, B$_3$ and B$_4$ contains at least one sulfo group.

7. The photochemical measurement method of claim 5 wherein said compound of formula (S) is represented by formula (S-II):

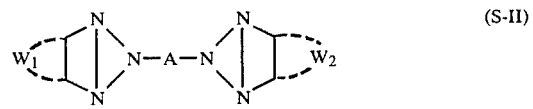

wherein A is a divalent aromatic residue, W$_1$ and W$_2$ each represents the carbon atom group necessary to complete a benzene ring or a naphthalene ring, wherein said benzene or naphthalene ring may be substituted with a substituent(s) and at least one of said substituents contains a sulfo group.

8. An analysis element for the photochemical measurement of a trace component (s) utilizing an immunological reaction which comprises, in succession, labelling an antigen or antibody with a spectral sensitizer, competitively reacting said antigen or antibody labelled with a spectral sensitizer and an antigen or antibody to be measured with an antibody or antigen which specifically reacts with the respective antigen or antibody, bringing either the reaction product or the unreacted component into contact with silver halide, exposing the resulting product to light having a wavelength which said spectral sensitizer absorbs, photographically developing the exposed silver, and measuring the resulting optical density of the formed silver image and/or colored dye formed by the photographic development, comprising a support having provided thereon a light sensitive layer containing said silver halide and said contact with said silver halide being performed in the presence of a hydrazine compound of formula (H):

(H)

wherein $R^{1h}$ is an aryl group and $R^{2h}$ is a hydrogen atom, an alkyl group or an aryl group, wherein said hydrazine compound is incorporated into the silver halide light sensitive material in the range of from $10^{-8}$ to $10^{-1}$ mol/mol Ag.

* * * * *